(12) United States Patent
Lundberg et al.

(10) Patent No.: US 12,576,106 B2
(45) Date of Patent: *Mar. 17, 2026

(54) COMPOSITIONS OF NITRATES AND METHODS OF USE THEREOF

(71) Applicant: Heartbeet Ltd., Ashbocking Ipswich (GB)

(72) Inventors: Jon Lundberg, Djursholm (SE); Eddie Weitzberg, Stockholm (SE)

(73) Assignee: HEARTBEET LTD., Ashbocking (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/660,160

(22) Filed: May 9, 2024

(65) Prior Publication Data

US 2024/0285678 A1 Aug. 29, 2024

Related U.S. Application Data

(60) Continuation of application No. 18/450,152, filed on Aug. 15, 2023, which is a continuation of application
(Continued)

(30) Foreign Application Priority Data

Feb. 26, 2007 (SE) .................................... 0700520-0
Mar. 22, 2007 (SE) .................................... 0700729-0

(51) Int. Cl.
*A61K 33/00* (2006.01)
*A23L 2/02* (2006.01)
(Continued)

(52) U.S. Cl.
CPC ................ *A61K 33/00* (2013.01); *A23L 2/02* (2013.01); *A23L 2/52* (2013.01); *A23L 33/105* (2016.08);
(Continued)

(58) Field of Classification Search
CPC ........ A61K 33/00; A61K 33/14; A61K 31/05; A61K 31/198; A61K 31/375; A61K 33/30;
(Continued)

(56) References Cited

U.S. PATENT DOCUMENTS 4,702,922 A 10/1987 Wiesenberger
4,853,237 A 8/1989 Prinkkila
(Continued)

FOREIGN PATENT DOCUMENTS

EP 0511587 A1 11/1992
EP 1747786 1/2007
(Continued)

OTHER PUBLICATIONS

Rahmouni et al., "Obesity-Associated Hypertension", Hypertension, vol. 45, Issue 1, pp. 9-14 (Year: 2005).*
(Continued)

*Primary Examiner* — Bethany P Barham
*Assistant Examiner* — Ayaan A Alam
(74) *Attorney, Agent, or Firm* — Booth Udall, PLC; Pacer K. Udall

(57) ABSTRACT

Disclosed is a method of administering nitrate in an effective and safe amount to cause a beneficial effect in a subject in need thereof. The method includes administering to the subject at least 0.01 mmol/kg/day of nitrate.

23 Claims, 13 Drawing Sheets

Related U.S. Application Data

No. 17/308,007, filed on May 4, 2021, now Pat. No. 11,723,917, which is a division of application No. 17/061,321, filed on Oct. 1, 2020, now Pat. No. 11,083,747, which is a continuation of application No. 15/966,508, filed on Apr. 30, 2018, now Pat. No. 10,842,813, which is a continuation-in-part of application No. 12/528,794, filed as application No. PCT/SE2008/050212 on Feb. 26, 2008, now Pat. No. 10,406,118, said application No. 15/966,508 is a continuation-in-part of application No. 14/830,937, filed on Aug. 20, 2015, now Pat. No. 10,555,968, which is a continuation of application No. 12/528,798, filed as application No. PCT/SE2008/050211 on Feb. 26, 2008, now Pat. No. 9,180,140.

(60) Provisional application No. 60/919,709, filed on Mar. 22, 2007.

(51) Int. Cl.

| | |
|---|---|
| *A23L 2/52* | (2006.01) |
| *A23L 33/105* | (2016.01) |
| *A23L 33/135* | (2016.01) |
| *A23L 33/16* | (2016.01) |
| *A61K 9/00* | (2006.01) |
| *A61K 9/08* | (2006.01) |
| *A61K 31/198* | (2006.01) |
| *A61K 31/375* | (2006.01) |
| *A61K 33/14* | (2006.01) |
| *A61K 33/30* | (2006.01) |
| *A61K 36/185* | (2006.01) |
| *A61K 36/21* | (2006.01) |
| *A61K 36/74* | (2006.01) |
| *A61K 45/06* | (2006.01) |
| *A61P 9/12* | (2006.01) |
| *C01D 9/00* | (2006.01) |

(52) U.S. Cl.
CPC ............. *A23L 33/135* (2016.08); *A23L 33/16* (2016.08); *A61K 9/0056* (2013.01); *A61K 9/0095* (2013.01); *A61K 9/08* (2013.01); *A61K 31/198* (2013.01); *A61K 31/375* (2013.01); *A61K 33/14* (2013.01); *A61K 33/30* (2013.01); *A61K 36/185* (2013.01); *A61K 36/21* (2013.01); *A61K 36/5777* (2024.05); *A61K 36/742* (2024.05); *A61K 45/06* (2013.01); *A61P 9/12* (2018.01); *A23V 2002/00* (2013.01); *C01D 9/00* (2013.01)

(58) Field of Classification Search
CPC .... A61K 36/185; A61K 36/21; A61K 9/0056; A61K 9/0095; A61K 9/08; A61K 45/06; A23V 2002/00; C01D 9/00; A23L 33/105; A23L 33/16; A23L 33/135; A23L 2/02; A23L 2/52; A61P 9/12
See application file for complete search history.

(56) References Cited

U.S. PATENT DOCUMENTS

| | | | |
|---|---|---|---|
| 4,868,179 A | 9/1989 | Cohn | |
| 5,476,847 A | 12/1995 | Mckittrick | |
| 6,024,992 A | 2/2000 | Yoo | |
| 6,117,872 A | 9/2000 | Maxwell | |
| 6,348,465 B1 | 2/2002 | Baker | |
| 6,419,900 B2 | 7/2002 | Placke | |
| 6,689,403 B1 | 2/2004 | Gehring | |
| 6,890,529 B1 | 5/2005 | Maeyrae-Maekinen | |
| 8,303,995 B1 | 11/2012 | Bryan | |
| 9,180,140 B2 | 11/2015 | Lundberg | |
| 10,406,118 B2 | 9/2019 | Lundberg | |
| 10,555,968 B2 | 2/2020 | Lundberg | |
| 10,821,132 B2 | 11/2020 | Lundberg | |
| 10,842,813 B2 | 11/2020 | Lundberg | |
| 11,083,747 B2 | 8/2021 | Lundberg | |
| 11,723,917 B2 | 8/2023 | Lundberg | |
| 2002/0110512 A1 | 8/2002 | Rigby | |
| 2003/0010459 A1 | 1/2003 | Farrar | |
| 2003/0036565 A1 | 2/2003 | Parkin | |
| 2003/0104596 A1 | 6/2003 | Mukerji | |
| 2003/0235571 A1 | 12/2003 | Gojon-Romanillos | |
| 2004/0016479 A1 | 1/2004 | Mullay | |
| 2004/0164479 A1 | 8/2004 | Shin | |
| 2004/0204371 A1 | 10/2004 | Cohn | |
| 2005/0036949 A1 | 2/2005 | Tucker | |
| 2005/0036996 A1 | 2/2005 | Roussel | |
| 2005/0226906 A1 | 10/2005 | Moneymaker | |
| 2005/0256192 A1 | 11/2005 | Gardiner | |
| 2005/0266018 A1 | 12/2005 | Boreyko | |
| 2006/0057118 A1 | 3/2006 | Toride | |
| 2006/0182815 A1 | 8/2006 | Gladwin | |
| 2007/0010581 A1 | 1/2007 | Esteve-Soler | |
| 2007/0071871 A1 | 3/2007 | Shrikhande | |
| 2007/0105817 A1 | 5/2007 | Page | |
| 2008/0226737 A1 | 9/2008 | Azria | |
| 2010/0047344 A1 | 2/2010 | Lundberg | |

FOREIGN PATENT DOCUMENTS

| | | | | |
|---|---|---|---|---|
| EP | 2008661 A2 | 12/2008 | | |
| GB | 962209 A | 7/1964 | | |
| JP | 05252905 | 10/1993 | | |
| JP | 2004305088 | 11/2004 | | |
| JP | 2010519336 | 6/2010 | | |
| KR | 20020057695 A | 7/2002 | | |
| WO | 199945797 | 9/1999 | | |
| WO | 9966921 | 12/1999 | | |
| WO | 2004017955 | 3/2004 | | |
| WO | WO-2004056376 A1 * | 7/2004 | .......... | A61K 31/616 |
| WO | 2005004884 A2 | 1/2005 | | |
| WO | 2005062713 | 7/2005 | | |
| WO | 2006110601 | 10/2006 | | |
| WO | 2006110601 A2 | 10/2006 | | |
| WO | 2007014334 A2 | 2/2007 | | |
| WO | 2007077210 | 7/2007 | | |

OTHER PUBLICATIONS

Mokdad et al., "Prevalence of Obesity, Diabetes, and Obesity-Related Health Risk Factors, 2001", JAMA, vol. 289, No. 1, pp. 76-79 (Year: 2003).*

Wood et al., "Effect of Adding Nitrate or Nitrite to Drinking Water on the Utilization of Carotene by Growing Swine", Journal of Animal Science, vol. 26, Issue 3, pp. 510-513 (Year: 1967).*

"Beneficial", "Benefit", Merriam-Webster.com Dictionary, Merriam-Webster, https://www.merriamwebster.com/dictionary/benefit. Accessed Sep. 6, 2024. (Year: 2024).*

"Meat and meat products—Determination of nitrate contact (Reference method)", International Standard ISO 3091, Ref. No. ISO 3091-1975(E), 1975.

A Butler et al., Medieval Chinese Medicine: The Dunhuang Medical Manuscripts (Chapter 16: A treatment for carenovascular dysfunction in a Dunhuang medical manuscript), Routledge (2005) 14 pages.

AJ Webb et al., "4.2 Acute blood pressure (BP) lowering and vasoprotective effects of beetroot juice: relationship to nitrite derived from dietary nitrate", Journal of Human Hypertension, vol. 21, No. 10, pp. 834-835. (Year 2007).

AJ Webb, et al., BHS Abstracts, Journal of Human Hypertension, vol. 21, pp. 828-850 (Sep. 20, 2007).

Appel et al., "A Clinical Trial of the Effects of Dietary Patterns on Blood Pressure", The New England Journal of Medicine, 336(16): 1117-1124, 1997.

(56) References Cited

OTHER PUBLICATIONS

Archer, Douglas L., Evidence that Ingested Nitrate and Nitrite Are Beneficial to Health, Journal of Food Protection, vol. 65, No. 5, pp. 872-875 (2002).

B. C. Challis, Nutrition and nitrosamine formation, Proceeds of the Nutrition Society, vol. 44, pp. 95-100 (1985).

B. Spiegelhalder, et al., Influence of Dietary Nitrate On Nitrate Content of Human Saliva: Possible Relevance of N-Nitroso Compounds, Fd. Cosmet. Toxicol., vol. 14, pp. 545-548 (1976).

B. Symonds, The Influence of Overweight and Underweight on Vitality, Journal of the Medical Society ofNew Jersey, vol. V, No. 4, pp. 159-167 (Sep. 1908)).

Bailey et al. "Dietary nitrate supplementation reduces the 02 cost of low-intensity exercise and enhances tolerance to ligh-intensity exercise in humans", J. Appl. Physiol., 2009, vol. 107, pp. 1144-1155. (Year 2009).

Balzer, et al., Reductase activity of polyphenols?: A commentary on 'Red wine-dependent reduction of nitrite to nitric Oxide in the stomach', Free Radical Biology and Medicine 43:1226-128,2007.

Benjamin, Nigel, Nitrates in the Human Diet—good or bad?, Ann. Zootech. vol. 49, pp. 207-216 (2000).

Bescos et al., The Effect of Nitric-Oxide-related Supplements on Human Performance, Sports Med, 42 (2):99-117 2012).

Bescos, "Effects of dietary L-Arginine intake on cardiorespiratory and metabolic adaptation in athletes", Int J Sport Nutr Exerc Metab, 19:355-65 (2009).

Bjone et al., Nitrite in Saliva Increases Gastric and Mucosal Blood Flow and Mucus Thickness, J. Clin. Invest. 113:106-114, Jan. 2004.

Bjorne, The Nitrite Ion: Its Role in Vasoregulation and Host Defenses, from the Department of Physiology and Pharmacology Section of Anesthesiology and Intensive Care medicine, Karolinska Instititutet, Stockholm, Sweden, pp. 1-66 (2005).

Boguslavskiy. Effect of nitric oxide on the efficiency of oxygen usage by a working skeletal muscle under fatigue, Fiziol. Zhum., vol. 51, No. 1, pp. 33-42 (2005) & Certified Translation.

British Medical Journal Webpage for EX1032 Article, 1909.

Bryan et al., Free Radical Biology & Medicine 41, pp. 691-701 2006.

Burtscher. The Proonged Intake of L-Arginine-L-Aspartate Reduces Blood Lactate Accumulation and Oxygen Consumption During Submaximal Exercise, Journal of Sports Science and Medicine, vol. 4, pp. 314-322 (2005).

Cederqvist et al., Direct Demonstration of NO Formation In Vivo From Organic Nitrites and Nitrates, and Correlation to Effects of Blood Pressure and to In Vitro Effects, Biochemical Pharmacology, vol. 47, No. 6, pp. 1047-1053, 1994.

Ceremuzynski et al., Effect of Supplemental Oral L-Arginine on Exercise Capacity in Patients with Stable Angina Pectoris, The American Journal of Cardiology, vol. 80, pp. 331-333,1997.

Chong, Relationship Between Circulating levels of Nitrates and Steroid in Patients Admitted to Coronary Care Unit, a hesis submitted to fulfill the requirements of the Degree of Master of Science to the Chinese University of Hong Kong, 2002.

Classen et al., Journal of the American College of Nutrition, vol. 9. No. 5. 500-502 (1990).

Cohn, et al., A Comparison of Enalapril with Hydralazine-Isosorbide Dinitrate in the Treatment of Chronic Congestive Heart Failure, The New England Journal of Medicine, 325:303-310 (1991).

Crawford et al., Effect of nitrate on determinants of myocardial oxygen consumption during exercise, International Journal of Cardiology, 1, 307-314,1982.

Crawford et al., Hypoxia, Red blood Cells, and Nitrite Regulate NO-dependent Hypoxic Vasodilation, Blood 2006, 107:566-574.

D. D. Rees, et al., Role of endothelium-derived nitric oxide in the regulation of blood pressure, Proc. Natl. Acad. Sci. USA, vol. 86, pp. 3375-3378 (May 1989).

Davidson et al., (2006). Effect of NO onmitochondhal function in cardiomyocytes: Pathophysiological relevance, Cardiovascular Research 71:10-21.

De Vries et al., Lactobacillus plantarum-survival, functional and potential probiotic properties in the human intestinal tract, International Dairy Journal, vol. 16, No. 9, Sep. 2006, pp. 1018-1028.

Deng et al., "Formation of ethyl nitrite in vivo after ethanol administration", Alcohol, Pergamon Press London, GB, vol. 34, No. 2-3, Oct. 1, 2004 (Oct. 1, 2004), pp. 217-223, XP004765251, ISSN: 0741-8329,001:10.1016/J.Mcohol.2004.09.005; abstract.

E.G. Heisler, et al., Changes in Nitrate and Nitrite Content, and Search/or Nitrosamines in Storage—Abused Spinach and Beets, J. Agr. Food Chem., vol. 22, No. 6, pp. 1029-1032 (1974).

Extra Strength Alka Seltzer Drug Facts (2004) (available at https://web.archive.org/web/ 20040422223603/http://www.alka-seltzer.com/as/ images/ Alka-Extra-Strength.gif.

F. Murad, Cyclic Guanosine Monophosphate as a Mediator of Vasodilation, J. Clin. Invest., vol. 78, pp. 1-5 (Jul. 1986).

Facts About The DASH Diet, U.S. Dept. of Health and Human Services; National Institutes of Health; National Heart, Lung, and Blood Institute (2001).

Ferrannini, Metabolism, 37(3):287-301 (1988).

Foex, P., "Hypertension: pathophysiology and treatment", Continuing Education in Anaesthesia, Critical Care & Pain, 4(3):71-75, 2004.

Friberg et al., Journal of Hypertension, 4(2): 165-173 (1986), Abstract only.

Fryer etal, "Mean Body Weight, Height, Waist Circumference, and Body Mass Index Among Adults: United States, 1999-2000 Through 2015-2016", US Dept of Health and Human Services, Centers for Disease Control and Prevention National Center for Health Statistics, No. 122, 2018.

G. M. McKnight, et al., Chemical synthesis of nitric oxide in the stomachfi-om dietary nitrate in humans, Gut, vol. 40, pp. 211-214 (1997).

G. R. J. Thatcher, Serial Review: Mechanisms and Novel Directions in the Biological Applications of Nitric Oxide Donors, Free Radical Biology & Medicine, vol. 37, No. 8, pp. 1122-1143 (2004).

Gago et al., Red wine-dependent reduction of nitrite to nitric oxide in the stomach, Free Radical Biology and Medicine 43:1233-1242, 2007. 10 pages.

Galley et al., Clin. Sci., 92, pp. 361-365 (Year: 1997).

Giulivi et al. (2006). Nitric oxide reduction of mitochondrial oxygen consumption I: cellular physiology, American Journal of Physiology—Cell Physiology 291:225-231.

Gladwin et al., Nature Chemical Biology, vol. 1 No. 6 Nov. 2005, pp. 308-314 (2005).

Gokce, L-Arginine and Hypertension, J. Nutr. 134: 2807S-2811S, 2004.

Grossi et al., A New Synthesis of Alkyl Nitrites: The Reaction of Alkyl Alcohols with Nitric Oxide in Organic Solvents, Journal of Organic Chemistry 64:8076-8079, 1999.

Grudzinski et al., Arch Environ Contam Toxicol. Sep. 1991;21 (3):468-74.

Grudzinski et al., Arch Environ Contam Toxicol. Sep. 1991;21(3):462-467.

Guazzi et al., The American Journal of Cardiology, 84:1038-1043 (1999).

Hamel et al., Critical Care Nurse, 31 (1 ):72-82 (2011).

Harrison, D.G. et al., "The Nitrovasodilators, new Ideas About Old Drugs," Circulation, vol. 87, No. 5, May 1993, pp. 1461-1467).

Hasegawa et al., J. Hypertension, 22, p. S200, abstract (Year: 2004).

Heusch et al., Endogenous Nitric Oxide and Myocardial Adaption to Ischemia, Circ. Res. 2000; 87:146-152, 2000.

Hunter et al., Nature Medicine, vol. 10, Oct. 2004, pp. 1122-1127.

Ijima et al., Gastroenterology, 122: 1248-1257 (2002).

Imaizumi. Effects of L-Arginine on Forearm Vessels and Responses to Acetylcholine, Hypertension, vol. 20, No. 4, pp. 511-517 (Oct. 1992).

J. Abrams, MD, Beneficial Actions of Nitrates in Cardiovascular Disease, The American Journal of Cardiology, vol. 77, pp. 31C-37C (May 30, 1996).

J. Warner, Nitrates Lower Blood Pressure: Nutrient Found in Spinach, Other Vegetables Keeps Blood Vessels Healthy, WebMD

(56) References Cited

OTHER PUBLICATIONS

Medical News (Dec. 27, 2006) (available at https://web.archive.org/web/ 20070119154017/htts://www.webmd.com/content/article/131/117916).

Journal of Human Hypertension Webpage for EXI 042, Oct. 2007, 2 pages.

Joyner et al., "Endurance exercise performance: the physiology of champions", J. Physiol, 586(1), pp. 35-44, published online Sep. 27, 2007. (Year: 2007).

Jungersten et al., "Both physical fitness and acute exercise regulate nitric oxide formation in healthy humans" Journal of Applied Physiology: Respiratory, Environmental and Exercise Physiology, American Physiological Society, US, vol. 82, No. 3, Jan. 1, 1997 (Jan. 1, 1997), pp. 760-764, XP003023021, ISSN: 0161-7567; abstract.

K Akhilender Naidu, Vitamin C in human health and disease is still a mystery? An overview, Nutrition Journal, vol. 2. No. 7 (2003).

K. Cosby, et al., Nitrite reduction to nitric oxide by deoxyhemoglobin vasodilates the human circulation, Nature Medicine, vol. 9, No. 12, pp. 1498-1505(Dec. 2003).

K. Tsuchiya, et al., Malfunction of Vascular Control in Lifestyle-Related Diseases: Formation of Systemic Hemoglobin-Nitric Oxide Complex (HbNO) From Dietary Nitrite, J. Pharmacol Sci, vol. 96, pp. 395-400 (2004).

Kahn, Anannas, Khazaain-al-Advia, vol. II (20th centurAD), Nadeem Yunus Printer/Sheikh Mohd Basheer & Sons, Lahore, 1911 AD, pp. 627-628, and translation.

Kelly et al.,Effect of short term dietary nitrate supplementation on blood pressure, 02 uptake kinetics, and muscle and cognitive function in older adults, Am J Physiol Regul Integr Comp Physiol., 304(2):R73-83 (2013).

Kirk et al. (Ann. Emerg. Med., Sep. 1993; 22 :1413-1418.).

L. Brunton, An Address on Blood Pressure In Man: Its estimation and indications for treatment, The British Medical Journal, pp. 64-67 (Jul. 10, 1909).

L. Brunton, et al., An Address on Longevity and the Means of Attaining It, The Lancet, vol. 168, Issue 4342, pp. 1330-1335 (Nov. 17, 1906).

Lacerda et al., Neuroscience Letters, 393, pp. 260-263 (2006).

Lansley et al., Dietary nitrate supplementation reduces the 02 cost of walking and running: a placebo-controlled study, J Appl Physiol., 110(3):591-600 (2011).

Larsen et al., "Effects of Dietary Nitrate on Oxygen Cost During Exercise," Acta Physiol. 191: 59-66, 2007.

Larsen et al., "Dietary inorganic nitrate improves mitochondrial efficiency in humans", Cell Metab., 13(2): 149-159 Feb. 2011).

Larsen, Effects of dietary nitrate on blood pressure in healthy volunteers, New England Journal of Medicine 355:2792-2793 (2006).

Laycock et al., Role of Nitric Oxide in the Control of Renal Oxygen Consumption in the Regulation of Chemical Work n the Kidney , Circ. Res., 82:1263-1271, 1998.

Liu et al., "No effect of short-term arginine supplementation on nitric oxide prduction, metabolism and performance in Intermittent exercise in athletes", J Nutr Biochem 20 (6): 462-468 (2008).

Lundberg et al., Arterioscler. Thromb. Vase. Biol., 25:915-922 (2005).

Lundberg, "Inorganic Nitrate is a Possible Source for Systemic Generation of Nitric Oxide," Free Radical Biology & Medicine,vol. 37, No. 3, pp. 395-400, 2004.

M Hermann et al., "Nitric Oxide in Hypertension", The Journal of Clinical Hypertension, Supp. 4, vol. 8, No. 12, pp. 17-29. (Year: 2006).

M. Robinson, et al., Effects of antacid formulation on postprandial oesophageal acidity in patients with a history of episodic heartburn, Ailment Pharmacol. Therm., vol. 16, pp. 435-443 (2002).

M. Smiechowska, The Content of Nitrates V and III and Vitamin C In Juices Obtained fi-om Organic and Conventional Raw Materials, Polish Journal of Food and Nutrition Sciences, vol. 12/53, No. 2, pp. 57-61 (2003).

McKnight et al., "Review article: Dietary nitrate in man: friend or foe?", British Journal of Nutrition, 81:349-358, 1999.

Millar et al., Xanthine Oxidoreductase Catalyses the Reduction of Nitrates and Nitrite to Nitric Oxide Under Hypoxic Conditions, FEBS Letters 427, 225-228, 1998.

Mishra, Madhuradi Manduram, Siddaprayogalatika, Translated by Vd. Shivakaran Sharma Chhangani, Chaukhamba Orientalia (Varanasi), Ed. 2nd 2005, p. 203, and translation.

Modin et al., Nitrite-derived Nitric Oxide: a Possible Mediator of Acidic-Metabolic Vasodilation, Acta Physiol Scand, 171,9-16, 2001.

Moncada et al., "The L-Arginine: Nitric Oxide Pathway", Journal of Cardiovascular Pharmacology, 17(Suppl. 3):S1-S9, Raven Press, New York, 1991.

NIHWebpage showing availability of EX1056 (NIH2) as of Feb. 12, 2006 (available at https://web.archive.org/web/20060212100027 /http.7/www.nhlbi.nih.gov/guidelines/hypertension/jnc7full. htm).

Nisoli et al., Mitochondrial biogenesis in mammals: the role of endogenous nitric oxide, Science, 299(5608):896-899 2003).

Ogden et al., Mean Body Weight, Height, and Body Weight Index, United States 1960-2002, Advanced Data From Vital and Health StatisticsNo. 347 (2004).

Oldreive, C, Rice-Evans, C, "The Mechanisms for Nitration and Nitrotyrosine Formation in vitro and in vivo: Impact of Diet", Free Rad. Res., vol. 35, pp. 215-231, 2001.

Olek et al., "A Single oral intake of arginine does not affect performance during repeated Wingate anaerobic test", J Sports Med Phys Fitness, 50(1):52-56 (2010).

Osada et al. Cholesterol oxidation in meat products and its regulation by supplementation of sodium nitrite and apple polyphenol before processing. J Agric Food Chem. 2000; 48: 3823-9.

P. Santamaria, Nitrate in vegetables: toxicity, content, intake and EC regulation, Journal of the Science of Food and Agriculture, 86:10-17 (2006).

Parent et al., Nitroglycerin reduces myocardial oxygen consumption during exercise despite vascular tolerance, Am J Physiol Heart Circ Physiol 290: H1226-H1234, 2005.

Peri et al, "Apples increase nitric oxide production by human saliva at the acidic pH of the stomach: A new biological function for polyphenols with a catechol group?", Free Radical Biology and Medicine, Elsevier Science, US, (Sep. 1, 2005), vol. 39, No. 5, doi: 10.1016/J.FREERADBIOMED.2005.04.021, ISSN 0891-5849, pp. 668-681, XP005013096.

Pickering et al., Why Don't We Use Nitrates to Treat Older Hypertensive Patients?, Journal of Clinical Hypertension, vol. 7, No. 11, pp. 685-690 (Nov. 2005).

Poderoso et al., Nitric oxide Regulates Oxygen Uptake and Hydrogen Peroxide Release by the Isolated Beating Rat Heart, Am. J. Physiol. 274 (Cell Physiol. 43): C112-C119; 1998.

RediBeets™ Webpage (2006) (available at https:I /web.archive.org/web/20060206221 752/https:/I allonhealth.com/health-products/redibeets.htm).

Richardson et al., "The ingestion of inorganic nitrate increases gastric S-nitrosothiol levels and inhibits platelet function in humans", Nitric Oxide, 7:24-29, 2002.

Roy, D., Insulin stimulation of glucose uptake in skeletal muscles and adipose tissues in vivo is NO dependent, Am. J. Physiology, vol. 274, No. 4, pp. E692-E699 (Apr. 1998).

Sar et al., Effects of Combination of Nitrate with _1-4Galacto-oligosaccharides and Yeast on Methane Emissioni from Sheep, Asian-Aust. J. Anim.Sci., vol. 17 No. 1:73-79,2004.

Scardi, Chronic Treatment After Acute Myocardial Infarction: Which Drug for Which Patient? Nitrates, Journal of Cardiovascular Pharmacology 14 ( . 9): S84-S88, 1989.

ScienceDirect Webpage for EXI033, Nov. 1906, 2 pages.

Sharkey, B. J., Fitness and Work Capacity, Second Edition, USDA Forest Service, Technology & Development Program (Apr. 1997), pp. 9-18.

Shen et al., "Nitric oxide production and NO synthase gene expression contribute to vascular regulation during exercise.", Med Sci Sports Exerc, 27(8):1125-34, 1995.

(56)             References Cited

OTHER PUBLICATIONS

Shibata et al. (Jul. 22, 2005). Nitric oxide modulates oxygen consumption by arteriolar walls in rat skeletal muscle, American Journal of Physiology: Heart Circulation Physiology 289:H2673-H2679.

Shiva et al. (2007). Deoxymyglobin is a nitrite reductase that generates nitric oxide and regulates mitochondrial espiration, Circulation Research 100:654-661.

Siddhaprayogasamgrahah, Phalasava, Part II; Krishan Gopal Ayureda Bhawan, Edn 8th 1990, pp. 620-621, and translation.

Sies et al., Cocoa polyphenols and inflammatory mediators, Am. J. Clin. Nutr., vol. 81, No. 1pp. 304S-312S (2005).

Sobko et al., Am. J. Physiol. Gastrointest. Liver Physiol. 287(5):0993-0997 (Nov. 2004).

Stamler et al., Biochemistry of Nitric Oxide and Its Redox-Activated Forms, Science, vol. 258, Dec. 18, 1992, pp. 1898-1902.

Stokes et al., "Long-Term Effectiveness of Extended-Release Nitrate for the Treatment of Systolic Hypertension", Hypertension, 45:380-384, 2005.

Sunderland et al., V02max and ventilator threshold of trained cyclists are not affected by 28-day l-arginine supplementation, J Strength Cond Res, 25 (3):883-837 (2011).

Tabau et al., Cardiovascular Research, 21:606-614 (1987).

The Lancet Webpage for EX1033, Nov. 17, 1906, 5 pages.

The Seventh Report of the Joint National Committee on Prevention, Detection, Evaluation, and Treatment of High Blood Pressure, U.S. Dept. of Health and Human Services; National Institutes of Health; National Heart, Lung, and Blood Institute (2004).

Tian et al., Hypertension Research, 34:1221-1227 (2011).

Tsuchiya, Nitrite is an alternative souce of NO in vivo, Am. J. Physil. Heart Circ, Physiol 288: H2163-H2170,2004.

Vahatalo et al.,No effect of acute L-arginine supplementation on 0(2) cot or exercise tolerance, Eur J Appl Physiol. Feb. 20, 2013).

Vaisya, Palakyasidhamatsya, Vangasena, Edited Shankar Ialji Jain, Khemraj Shrikrishna Das Prakashan, Bombay, Edn. 1996, p. 1062, and translation.

Van Velzen et al., Toxicology Letters, 181:177-181 (2008).

Wayback Machine Archive of INCHEM Webpage entitled Nitrates and nitrites (archived Dec. 15, 2006).

Wayback Machine Archive of NIH Webpage defining "nutritional supplement" (archived Feb. 3, 2007)).

Wayback Machine Webpage for EXI 042 archived Oct. 11, 2007.

Weiqun Shen et al, "Role of Nitric Oxide in the Regulation of Oxygen Consumption in Conscious Dogs", Circulation Research, (Jan. 28, 1994), vol. 75, doi:10.1161/01.RES.75.6.1086, pp. 1086-1095, XP055198527.

Whisonant et al., "Geology and History of Confederate Saltpeter Dave Operations in Western Virginia", Virginia Minerals, 47(4):33-44, 2021.

White, Relative Significance of Dietary Sources of Nitrate and Nitrite, J. Agric. Food Chem., vol. 23, No. 5, 6 pages (1975).

Xu et al., Applied Microbiology and Biotechnology, vol. 56, No. 3-4, Aug. 2001, pp. 504-507.

Yoon et al., Bioresource Technology 97 (2006) 1427-1430.

Houston et al "Juice Powder Concetrate and Systemic Blood Pressure" eCAM, 4(4) 455-462 date: Feb. 7, 2007.

Toldam-Anderson et al "Growth and development in black currants" Journal of Horticultural sciences; 72(1) Jul. 20, 1996; p. 155-169.

Declaration of Jon Lundberg and Eddie Weitzberg Under 37 C.F.R. 1.132. Dec. 20, 2017.

Jones, Andrew M., et al., "Nitric oxide synthase inhibition with L-NAME reduces maximal oxygen uptake but not gas exchange threshold during incremental cycle exercise in man," J Physiol 560.1. 2004, pp. 329-338. 2004.

Tanaka, Hiroaki, et al., "Effect of Nifedipine, Dilazep, Dinitrates and Propranolol on Blood Lactate Accumulation during Intensive Graded Exercise Testing in healthy Young Subjects," Jpn Heart J. 1988, 617-630.

How To Boost Your Circulation (And Why It's So Important For Your Health), Henry Ford Health, Oct. 27, 2020.

NCI Dictionary of Cancer Terms, Nat'l Cancer Inst., https://www.cancer.gov/publications/dictionaries/cancer-terms/def/blood-circulation (last visited Sept. 9, 2025).

Mauricio Di Fulvio et al., Diuretics: A Review of the Pharmacology and Effects on Glucose Homeostasis, 16 Front. Pharmacol., art. 1513125, at 1(Mar. 27, 2025).

Jamadar, Moshin Jahangeer et al., Formulation Design and Evaluation of Chewable Tablet Containing Sucralfate and Diclofenac, 5 J. Med. & Pharm. Allied Sci. 198, 199 (2016).

Sharma, Arya M et al., b-Adrenergic Receptor Blockers and Weight Gain: A Systematic Analysis, 24 Obesity Revs. e13353, abstract (2023).

Fried, Terri R. et al., The Effects of Comorbidity on the Benefits and Harms of Treatment for Chronic Disease: A Systematic Review, 9 PLOS One e112593, at 3 (Nov. 2014).

* cited by examiner

COMPOSITIONS OF NITRATES AND METHODS OF USE THEREOF

RELATED APPLICATIONS

This application is a continuation application of earlier filed U.S. Utility patent application to Jon Lundberg and Eddie Weitzberg, titled "Compositions of Nitrates and Methods of Use Thereof," application Ser. No. 18/450,152, filed Aug. 15, 2023, now pending, which is a continuation application of earlier filed U.S. Utility patent application to Jon Lundberg and Eddie Weitzberg, titled "Compositions of Nitrates and Methods of Use Thereof," application Ser. No. 17/308,007, filed May 4, 2021, now issued as U.S. Pat. No. 11,723,917, which is a divisional application of earlier filed U.S. Utility patent application to Jon Lundberg and Eddie Weitzberg, titled "Compositions of Nitrates and Methods of Use Thereof," application Ser. No. 17/061,321, filed Oct. 1, 2020, now issued as U.S. Pat. No. 11,083,747, which is a continuation application of earlier U.S. Utility patent application to Jon Lundberg and Eddie Weitzberg, titled "Compositions of Nitrates and Methods of Use Thereof," application Ser. No. 15/966,508, filed Apr. 30, 2018, now issued as U.S. Pat. No. 10,842,813, which is a continuation-in-part application of earlier U.S. Utility patent application to Jon Lundberg and Eddie Weitzberg, titled "Use of Nitrites and Nitrates and Compositions Containing These," application Ser. No. 12/528,794, filed Aug. 26, 2009, now issued as U.S. Pat. No. 10,406,118, which is a national stage application of PCT Application No. PCT/SE08/50212, filed Feb. 26, 2008, which claims the benefit of the filing date of U.S. Provisional Patent Application 60/919,709 to Jon Lundberg and Eddie Weitzberg, filed on Mar. 22, 2007, the disclosures of all of which being hereby incorporated entirely herein by reference.

U.S. patent application Ser. No. 15/966,508 is also a continuation-in-part application of earlier U.S. Utility patent application to Jon Lundberg and Eddie Weitzberg, titled "Performance Enhancing Compositions and Use Thereof," application Ser. No. 14/830,937, filed Aug. 20, 2015, now issued as U.S. Pat. No. 10,555,968, which is a continuation application of earlier U.S. patent application Ser. No. 12/528,798, filed Aug. 26, 2009, now issued as U.S. Pat. No. 9,180,140, which was a national stage application of PCT application No. PCT/SE 2008/050211, filed Feb. 26, 2008, which claims priority to Swedish Patent Application 0700520-0, which was filed Feb. 26, 2007, and Swedish Patent Application 0700729-0, which was filed Mar. 22, 2007, the disclosures of all of which being hereby incorporated entirely herein by reference.

FIELD OF THE INVENTION

The present invention relates to the field of performance enhancing nutritional foods and food supplements, liquid and solid edible products such as sport drinks, energy drinks and energy bars. The present invention also relates to the field of medicine and pharmaceuticals, in particular pharmaceuticals and therapeutic methods for lowering metabolic rate, oxygen consumption and/or glucose homeostasis in a human patient or another mammal, based on the administration of nitrates and/or nitrites to said patient or mammal.

BACKGROUND OF THE INVENTION

NO is involved in control of cellular respiration through interaction with enzymes of the mitochondrial respiratory chain (for review see MONCADA, S, et al. Does nitric oxide modulate mitochondrial energy generation and apoptosis?. Nat Rev Mol Cell Biol. 2002, vol. 3, no. 3, p. 214-20). The classical means by which NO production occurs is the L-arginine pathway, where NO is synthesized by specific enzymes, the NO-synthases. A fundamentally different alternative way of generating NO has been described more recently (LUNDBERG, J O, et al. Intragastric nitric oxide production in humans: measurements in expelled air. Gut. 1994, vol. 35, no. 11, p. 1543-6; BENJAMIN, N, et al. Stomach NO synthesis. Nature. 7 Apr. 1994, vol. 368, no. 6471, p. 502; ZWEIER, J L, et al. Enzyme-independent formation of nitric oxide in biological tissues. Nat Med. 1995, vol. 1, no. 8, p. 804-9; and WEITZBERG, E, et al. Nonenzymatic nitric oxide production in humans. NO Biol. Chem. 1998, no. 2, p. 1-7). In this NOS-independent pathway the inorganic anions nitrate ($NO_3$) and nitrite ($NO.sub.2$--) are reduced in vivo to form NO. Dietary nitrate (found mainly in green leafy vegetables) (MCKNIGHT, G M. Chemical synthesis of nitric oxide in the stomach from dietary nitrate in humans. Gut. 1997, no. 40, p. 211-214; and Weitzberg, 1998, supra) is absorbed from the circulation by the salivary glands, secreted in saliva and partly converted to nitrite in the oral cavity by nitrate reducing bacteria. Swallowed nitrite can then enter the systemic circulation. Indeed, a recent study shows that ingestion of nitrate results in a sustained increase in circulating nitrite levels (LUNDBERG, J O, et al. Inorganic nitrate is a possible source for systemic generation of nitric oxide. Free Rad Bio Med. 2004, vol. 37, no. 3, p. 395-400). Further reduction of nitrite into bioactive NO can occur spontaneously in acidic or reducing environments (Benjamin et al. 1994, supra, Lundberg et al. 1994, supra) but is also greatly enhanced by various proteins and enzymes including deoxyhemoglobin in blood (COSBY, K, et al. Nitrite reduction to nitric oxide by deoxyhemoglobin vasodilates the human circulation. Nat Med. 2003, vol. 9, no. 12, p. 1498-505), deoxymyoglobin (SHIVA, S. et al. Deoxymyoglobin is a Nitrite Reductase That Generates Nitric Oxide and Regulates Mitochondrial Respiration. Circ Res. 9 Feb. 2007), xanthine oxidase (MILLAR, T M, et al. Xanthine oxidoreductase catalyses the reduction of nitrates and nitrite to nitric oxide under hypoxic conditions. FEBS Lett. 8 May 1998, vol. 427, no. 2, p. 225-8) and possibly by enzymes of the mitochondrial respiratory chain (for review see LUNDBERG, J O, et al. Nitrate, bacteria and human health. Nat Rev Microbiol. 2004, vol. 2, no. 7, p. 593-602; LUNDBERG, J O, et al. NO generation from nitrite and its role in vascular control. Arterioscler Thromb Vasc Biol. 2005, vol. 25, no. 5, p. 915-22; and GLADWIN, M T, et al. The emerging biology of the nitrite anion. Nat Chem. Biol. 2005, vol. 1, no. 6, p. 308-14). NOS-independent NO production seems to complement the endogenous NO production especially during ischemia and acidosis when oxygen availability is low and the NO synthases operate poorly (Zweier et al. 1995, supra; Weitzberg et al, 1998, supra; DURANSKI, M R, et al. Cytoprotective effects of nitrite during in vivo ischemia-reperfusion of the heart and liver. J Clin Invest. 2005, vol. 115, no. 5, p. 1232-40; Lundberg et al, 2004, supra). Tissue acidosis and relative hypoxia is present also during physical exercise and in this metabolic state, bioactivation of nitrite is likely enhanced.

Recent studies indicate that nitrate and nitrite can have significant biological effects in the body and that these effects may be beneficial (LUNDBERG, Jon O., et al. Nitrate, bacteria and human health. Nat Rev Microbiol. 2004, no. 2, p. 593-602). For example, the nitrite anion can cause vasodilatation at near physiological concentrations when tested in vitro (MODIN, A., et al. Nitrite-derived nitric oxide: a possible mediator of 'acidic-metabolic' vasodilation. Acta Physiol Scand. 2001, vol. 171, p. 9-16) or when infused intra-arterially to humans (COSBY, K., et al. Nitrite reduction to nitric oxide by deoxyhemoglobin vasodilates the human circulation. Nat Med. 2003, no. 9, p. 1498-505). Nitrate can be converted to nitrite in vivo in a process dependent on commensal bacteria (SPIEGELHALDER, B., et al. Influence of dietary nitrate on nitrite content of human saliva: possible relevance to in vivo formation of N-nitroso compounds. Food Cosmet Toxicol. 1976, no. 14, p. 545-548). When nitrate is ingested it is rapidly absorbed into blood and then accumulates in saliva. In the oral cavity bacteria reduce parts of the dietary nitrate to nitrite and nitrite can then enter the systemic circulation. (LUNDBERG, Jon O., et al. Inorganic nitrate is a possible source for systemic generation of nitric oxide. Free Radic Biol Med. 2004, vol. 37, p. 395-400).

In vitro studies published in the 1990s show that NO is a modulator of mitochondrial respiration via reversible inhibition of cytochrome c oxidase (CARR, G J. et al. Nitric oxide formed by nitrite reductase of *Paracoccus denitrificans* is sufficiently stable to inhibit cytochrome oxidase activity and is reduced by its reductase under aerobic conditions. Biochim Biophys Acta. 15 May 1990, vol. 1017, no. 1, p. 57-62; BOLANOS, J P, et al. Nitric oxide-mediated inhibition of the mitochondrial respiratory chain in cultured astrocytes. J. Neurochem. 1994, vol. 63, no. 2, p. 910-6; BROWN, G C, et al. Nanomolar concentrations of nitric oxide reversibly inhibit synaptosomal respiration by competing with oxygen at cytochrome oxidase. FEBS Lett. 19 Dec. 1994, vol. 356, no. 2-3, p. 295-8; CLEETER, M W, et al. Reversible inhibition of cytochrome c oxidase, the terminal enzyme of the mitochondrial respiratory chain, by nitric oxide. Implications for neurodegenerative diseases. FEBS Lett. 23 May 1994, vol. 345, no. 1, p. 50-4; and SCHWEIZER, M, et al. Nitric oxide potently and reversibly deenergizes mitochondria at low oxygen tension. Biochem Biophys Res Comm. 1994, no. 204, p. 169-75). NO may also interact at other sites of the mitochondrial respiratory chain and in the Krebs cycle (for review see Moncada, supra). While this important action of NO has been very well characterised in cell cultures, less is known about its physiological relevance in vivo. To date the focus among researchers has been on the cardiovascular effects of nitrite after its in vivo reduction to the vasodilator nitric oxide (NO) (COSBY et al. (supra); DURANSKI, M. R., et al. Cytoprotective effects of nitrite during in vivo ischemia-reperfusion of the heart and liver. J Clin Invest. 2005, vol. 115, p. 1232-1240; GLADWIN, M. T., et al. The emerging biology of the nitrite anion. Nat Chem Biol. 2005, no. 1, p. 308-14; LARSEN, F. J., et al. Effects of dietary nitrate on blood pressure in healthy volunteers. N Engl J Med. 2006, vol. 355, p. 2792-3). WO 2005/004884 A (US GOVERNMENT ET AL.) 2005 Jan. 20 and WO 2005/007173 A (US GOVERNMENT ET AL.) 2005 Jan. 27 describe a method to administer a nitrite salt specifically to obtain vasodilatation in a subject. No effects of low-dose nitrate/nitrite on energy expenditure or glucose homeostasis or the effects of NO on cellular respiration during physical exercise have been described.

Physiological adaptation to exercise involves major cardiovascular and metabolic changes. Oxygen consumption increases dramatically in the active muscles with a parallel increase in muscle blood flow. In these processes, the endogenous gas nitric oxide (NO) plays an important regulatory role. NO increases blood flow to the muscles and modulates muscular contraction and glucose uptake (for review see STAMLER, J S. et al. Physiology of nitric oxide in skeletal muscle. Physiol Rev. 2001, vol. 81, no. 1, p. 209-37).

The available information on the role of NO in healthy subjects and in particular in athletes during work or exercise is both insufficient and contradictory. Shen and colleagues showed that administration of NOS-inhibitors in vivo during submaximal exercise leads to increased oxygen consumption in dogs (SHEN, W. et al. Role of NO in the regulation of oxygen consumption in conscious dogs. Circulation Res. 1999, no. 84, p. 840-5) and Lacerda and colleagues showed similar results in rats (LACERDA, A C R, et al. Evidence that brain nitric oxide inhibition increases metabolic cost of exercise, reducing running performance in rats. Neuroscience Letters. 2006, no. 393, p. 260-3). The majority of studies have been done using NOS-inhibitors while the effects of administering exogenous NO on exercise are largely unknown. In addition, studies in healthy humans are scarce.

Interestingly, the marketing of some currently available food supplements for athletes and bodybuilders refer to the vasodilatory effect of NO. One example is "NOX2" (Bodyonics, Ltd., USA), a product said to contain arginine alpha-ketoglutarate (A-AKG) and arginine-ketoisocaproate (A-KIC) and allegedly capable of boosting short term nitric oxide levels. Other products contain L-arginine, from which NO is synthesized by the NOS enzymes, and the beneficial effects of NO are often referred to, however without offering more detailed explanations.

The relation between peak work rate and resting levels of nitrate in plasma and urine from subjects with different levels of physical fitness has been studied (Jungersten et al., Both physical fitness and acute exercise regulate nitric oxide formation in healthy humans. J Appl Physiol 82:760-764, 1997). A positive relationship between physical fitness and formation of NO at rest was found and it was hypothesised that this positive relationship helps to explain the beneficial effects of physical exercise on cardiovascular health. In Jungersten's study nitrate was used solely as a marker of NO production and the authors state several times that nitrate is a stable and inert end product of NO and that it is biologically inactive.

Nitrate ($NO_3^-$) and nitrite ($NO_2^-$) are generally viewed as unwanted residues in the food chain with potentially harmful effects (Joint FAO/WHO Expert Committee on Food Additives (JECFA). Safety Evaluation of Certain Food Additives. WHO, 1970. ISBN 9241660503; TANNENBAUM, S. R., et al. Nitrite in human saliva. Its possible relationship to nitrosamine formation. J cancer Ins. 1974, vol. 53, p. 79-84; BARTSCH, H., et al. Inhibitors of endogenous nitrosation: mechanisms and implications in human cancer prevention. Mutation Res. 1988, vol. 202, p. 307-324). Proposed harmful effects of these anions include promotion of gastric cancers and other malignancies and development of methemoglobinemia in infants. Because of this the levels of nitrate/nitrite are strictly regulated in food and drinking water.

SUMMARY OF THE INVENTION

The disclosure is directed to methods of promoting health in a human (healthy or non-healthy). The methods include administering inorganic nitrate ($NO_3^-$) to the human subject.

In one aspect, a method of administering nitrate in an effective and safe amount to cause a beneficial effect in a subject in need thereof is disclosed. The method includes administering to the subject between 0.01 mmol/kg/day and 100.0 mmol/kg/day of the nitrate.

In another aspect, a method of administering nitrate in an effective and safe amount to cause a beneficial effect in a subject in need thereof is disclosed. The method includes administering to the subject at least 0.01 mmol/kg/day of nitrate.

Implementations may include one or more or all of the following.

The nitrate is administered at a dose of 0.01 mmol/kg/day to 1.0 mmol/kg/day.

The amount of nitrate is at least 0.1 mmol/kg/day.

The amount of nitrate is administered in a single dose.

The amount of nitrate is administered in multiple doses per day. For example, the amount of nitrate is administered in three doses per day.

At least one dose of nitrate is administered before the onset of exercise. For example, the dose of nitrate is administered at about 60 minutes before exercise.

The beneficial effect is selected from the group consisting of: reduction in oxygen consumption, increase in endurance, increase in muscular efficiency, reduction in the oxygen cost of exercise, reduction in blood pressure, increase in vasodilation, increase in muscle blood flow, reduction of systolic blood pressure, reduction of diastolic blood pressure, and reduction of mean arterial blood pressure.

The beneficial effect is amelioration of a disease or condition associated with increased metabolic rate and/or oxygen consumption. For example, the disease or condition is selected from the group consisting of: surgical stress, malnutrition, burn injury, premature birth, anorexia, happenstance of organ transplantation, fasting hyperglycemia, impaired fasting glucose, impaired glucose tolerance, insulin resistance, reduced HDL cholesterol, elevated triglycerides, elevated uric acid, obesity, cancer with anorexia, diabetes, stroke, hypertension, hyperthyreosis, cardiac arrest, myocardial infarction, sleep apnea syndrome, organ ischemia, chronic obstructive pulmonary disorder, fever, and asthma.

The disease or condition is impaired glucose tolerance.

The disease or condition is diabetes.

The disease or condition is reduced HDL cholesterol.

The disease or condition is elevated triglyceride.

The disease or condition is obesity.

The disease or condition is fever.

The disease or condition is asthma.

Administering to the subject at least 0.01 mmol/kg/day of nitrate does not cause any significant increase of the methemoglobin level in the subject.

Administering to the subject at least 0.01 mmol/kg/day of nitrate does not cause methemoglobin formation greater than 10% in the subject.

Administering to the subject at least 0.01 mmol/kg/day of nitrate does not cause methemoglobin formation greater than 5% in the subject.

Administering to the subject at least 0.01 mmol/kg/day of nitrate does not cause methemoglobin formation greater than 2% in the subject.

Administering to the subject at least 0.01 mmol/kg/day of nitrate causes no methemoglobin formation.

Further aspects and implementations will become evident to the skilled person upon study of the figures, description and examples, as well as the appended claims, incorporated herein by reference.

DESCRIPTION OF THE FIGURES

The invention will be described in closer detail in the following description, examples and non-limiting claims, with reference to the attached drawings in which:

DETAILED DESCRIPTION

Figure 1:
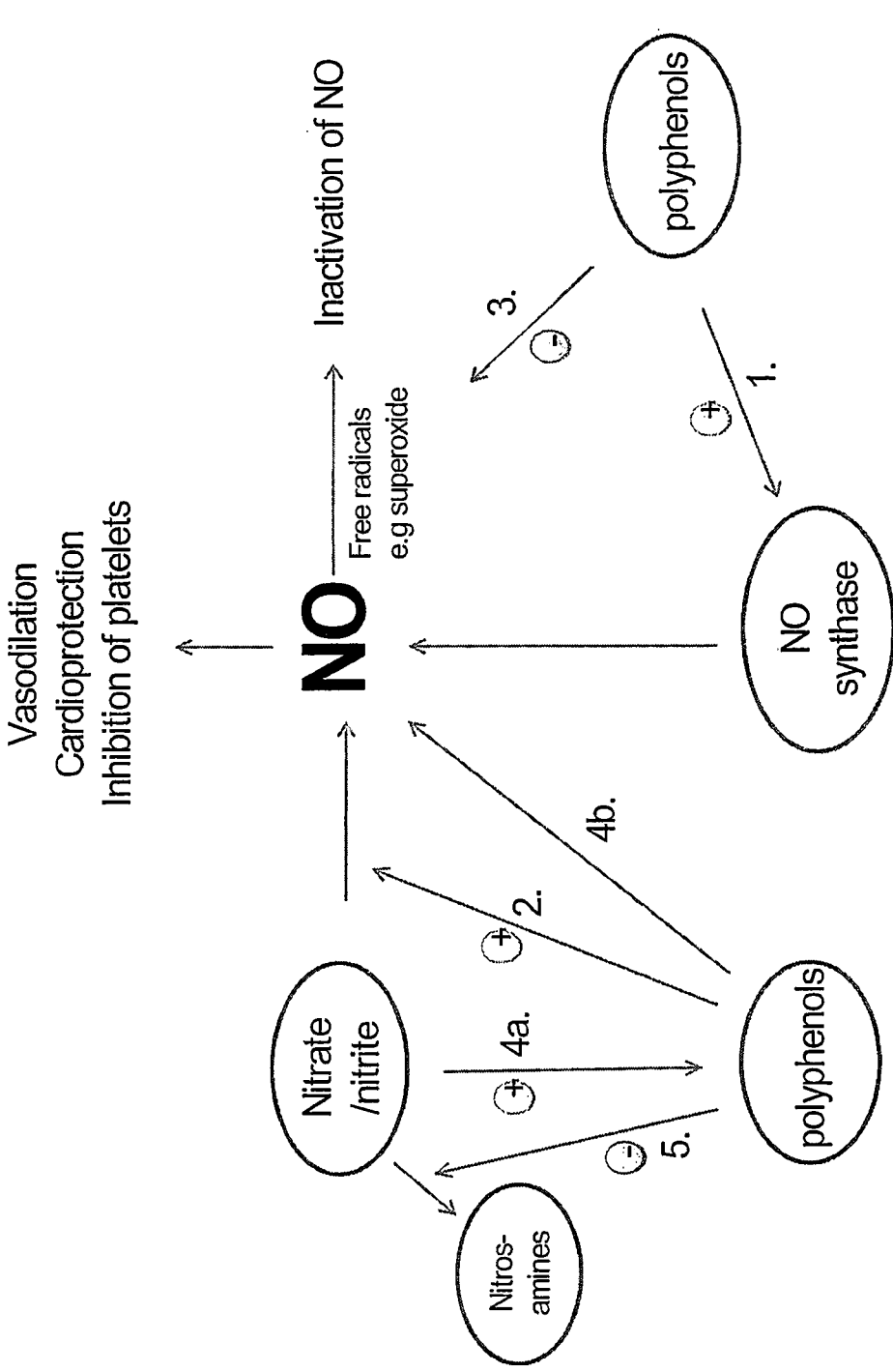
FIG. 1 shows a graph illustrating numerous ways in which the combination of nitrate and polyphenols synergistically act to increase the bioavailability of nitric oxide and at the same time to reduce the formation of harmful compounds such as oxygen radicals and nitrosamines. For detailed explanation see text.

Before the present method and compositions are described in the form of embodiments thereof, it is to be understood that this invention is not limited to the particular configurations, method steps, and materials disclosed herein as such configurations, steps and materials may vary somewhat. It is also to be understood that the terminology employed herein is used for the purpose of describing particular embodiments only and is not intended to be limiting since the scope of the present invention will be limited only by the appended claims and equivalents thereof.

It must also be noted that, as used in this specification and the appended claims, the singular forms "a," "an," and "the" include plural referents unless the context clearly dictates otherwise.

The term "about" when used in the context of numeric values denotes an interval of accuracy, familiar and acceptable to a person skilled in the art. Said interval can be +/−2% of the given value, preferably +/−5%, and most preferably +/−10% of the numeric values, where applicable.

The term "indirect calorimetry" is here defined as a method for calculating heat that living organisms produce from their production of carbon dioxide and nitrogen waste and from their consumption of oxygen, well known to persons skilled in the relevant art.

The term "catabolism" is defined as the metabolic process that breaks down molecules into smaller units. It is made up of degradative chemical reactions in the living cell.

The term "edible" in this context means non-toxic and possible to ingest, however not limited to particular modes of ingesting, such as drinking, chewing, applying to the oral cavity in various forms, such as, for example a spray or aerosol.

The term "energy expenditure" is here defined as the amount of energy expended for a certain metabolic rate.

The term "functional food" relates to any fresh or processed food claimed to have a health-promoting and/or disease-preventing property beyond the basic nutritional function of supplying nutrients. Functional foods are sometimes called nutraceuticals. The general category includes processed food made from functional food ingredients, or fortified with health-promoting additives, like "vitamin-enriched" products, and also, fresh foods (e.g. vegetables) that have specific claims attached. Fermented foods with live cultures are often also considered to be functional foods with probiotic benefits.

The term "insulin resistance" is here defined as a condition in which normal amounts of insulin are inadequate to produce a normal insulin response from fat, muscle and liver cells.

The term "mammal" is intended to encompass all mammals, and in particular humans, pets and agriculturally significant animals, as well as animals used in competitions, such as horses and dogs.

The term "metabolic syndrome" is here defined as a combination of medical disorders that increase the risk for cardiovascular disease and diabetes in a human. Symptoms and feature include fasting hyperglycaemia, diabetes mellitus type 2 or impaired fasting glucose, impaired glucose tolerance or insulin resistance, high blood pressure, central obesity, decreased HDL cholesterol, elevated triglycerides and elevated uric acid levels.

The term "metabolism" is used to define the complete set of chemical reactions that occur in living cells and "metabolic rate" is defined as the speed of metabolism of a mammal.

Methemoglobin is a form of hemoglobin in which the iron in the heme group is in the $Fe_3^+$ state, not the $Fe_2^+$ of normal hemoglobin. Methemoglobin is unable to carry oxygen. Methemoglobinemia is defined as a blood disorder characterized by the presence of a higher than normal level of methemoglobin in the blood.

The term "oxygen consumption" is defined as the amount of oxygen ($O_2$) consumed by a mammal and is usually expressed as ml of pure oxygen consumed/min. "Oxygen consumption" relates to the amount of oxygen consumed by a mammal as whole but also to oxygen consumption in an isolated tissue or organ, such as, but not limited to, heart, liver brain or other tissue exposed to ischemia.

The term "performance enhancing food or food supplement" includes sport drinks and energy drinks, as well as other liquid, semi-solid or solid forms, such as energy bars and tablets. No distinction is intended between sports drinks and energy drinks. Sports drinks tend to be more isotonic while energy drinks tend to contain more sugar and frequently also contain caffeine. Usually, sports drinks are non-carbonated and frequently contain fructose or other sugars, and complex carbohydrates, which are easily absorbed by the body, and are designed to promote the availability of energy and/or prevent or treat mild dehydration. Sport drinks also contain electrolytes (mainly sodium and potassium salts) and nutrients (proteins and amino acids). Sport drinks, energy drinks and other liquid, semi-solid and solid products, while marketed for athletes, are also consumed by non-athletes, as a snack, in situations where extra energy and endurance is desired. It is currently believed that improved sports performance can be attained by the intake of so-called sport drinks.

The term "significant hypotension" means in this context an acute reduction of systolic and/or diastolic blood pressure, accompanied by clinical symptoms of hypotension such as dizziness, nausea, pallor, loss of consciousness, etc. Said symptoms may occur in various degrees, and it is preferred that they are entirely avoided, minimized or eliminated as far as possible, or at least to an extent that they are clinically insignificant.

The inventors have surprisingly shown that the metabolic rate and/or the oxygen consumption can be influenced in a mammal (locally or systemically), by administering inorganic nitrite ($NO_2^-$) and/or nitrate ($NO_3^-$) to said mammal in an amount of nitrite and/or nitrate sufficient to decrease oxygen consumption. The decreased oxygen consumption is achieved without causing significant hypotension and without causing any significant increase of the methemoglobin level in said mammal. In case of local reduction of the metabolic rate, the oxygen consumption is decreased in an isolated tissue or organ such as the heart, liver, brain or other tissue that is exposed to ischemia (a condition in which blood flow, and thus oxygen, is restricted to a part of the body). In such cases the interaction of reaction products (including NO) of nitrite and/or nitrate with enzymes of the mitochondrial respiratory chain and subsequent inhibition of respiration leads to lowering of oxygen demand, which is beneficial for an ischemic tissue. This effect resembles hibernation. Because the generation of active nitrite and/or nitrate reaction products is maximized in ischemic tissues the effect of oxygen consumption will be most pronounced at these sites. In one particular embodiment, the oxygen consumption is lowered in the heart.

The inventors also showed that dietary supplementation with inorganic nitrate results in a reduced $VO_2$ during physical exercise and a significant increase in muscular efficiency. These effects occurred without any increase in plasma lactate.

In principle, also other additional approaches can lead to increased systemic or local nitrite levels. The most obvious is to administer nitrite or its precursor nitrate as such, but this may be supplemented by or enhanced by increasing the gastric pH (e.g. with an acid suppressive drug such as a proton pump inhibitor or $H_2$ receptor antagonist or antacids) to maximize nitrite survival in the stomach and thereby the systemic delivery of nitrite. Alternatively, the administration of nitrite or nitrate can be supplemented by or enhanced by interfering with the oral microflora in order to maximize the number of nitrate reducing species. This can be achieved through the delivery of "probiotic" nitrate reducing bacteria or selective treatment with an antibiotic to favor the nitrate reducing species.

The surprising finding that nitrite and its precursor nitrate affects such vital physiological processes as metabolic rate and/or oxygen consumption can be used therapeutically, e.g. in prophylaxis, alleviation or treatment of several conditions. In an attempt to increase systemic nitrite levels, nitrite and/or nitrate can be given by enteral administration (orally, in the form of a liquid, semi-solid or solid preparation, such as a chewing gum, tablet, lozenge, wafer, cake, bar or the like) or by parenteral administration (intravenous, transdermal, transcutaneous, by inhalation, rectally, vaginally, topical, intraperitoneally, intra muscular, subcutaneous, sublingual or any other way of parenteral administration). The nitrite and/or nitrate comprising composition and possible further combinations described herein can be administered continuously or as single bolus doses. In some aspects, the inventors make available a composition, preferably an edible composition, capable of enhancing performance manifested as a reduced oxygen uptake ($VO_2$) during physical exercise when ingested by a mammal, wherein said composition comprises inorganic nitrate and/or nitrite, and in particular a composition wherein the effect of enhanced performance is manifested as both a reduced oxygen uptake ($VO_2$) during physical work and a significant increase in muscular efficiency.

Composition

It is likely that an optimal dose-interval exists, meaning that below a certain plasma level of nitrite the effects are insufficient and, correspondingly, that over a certain level the effect is lower and possibly accompanied by side effects. In one embodiment, the composition comprising inorganic nitrite and/or nitrate is a pharmaceutical composition comprising inorganic nitrite and/or nitrate in an amount which is sufficient to decrease oxygen consumption, but which does not increase the methemoglobin level in a subject when administered to said subject in a prescribed dose. Optionally the composition comprises another pharmaceutically active compound.

According to a particular embodiment, said composition comprises nitrite alone, without the presence of nitrate. According to another embodiment, said composition in addition to nitrate and/or nitrite, also comprises arginine.

According to one embodiment, nitrate and nitrite are given in a dose ratio interval of about 5:1 to about 100:1 (nitrate:nitrite), such as 5:1, 10:1, 30:1, 50:1, 70:1 and 100:1. Preferably the dose ratio is about 10:1. This will ensure acute effects of the nitrite as soon as it is absorbed, and then provide a sustained effect of the nitrate following its bioconversion into nitrite.

Preferably the dose of nitrate is about 1-1000 umol sodium nitrate/kg bodyweight/day. Correspondingly, the dose of nitrite is preferably about 0.1-100 umol/kg bodyweight/day. More specifically, for the use of a nitrate salt perorally, a dose of about 0.01-100 mmol/kg/24 h is currently preferred or more preferably a dose of about 0.01-10 mmol/kg/24 h, even more preferably 0.1-1 mmol/kg/24 h. Correspondingly, the dose of nitrite is about 0.001-10 mmol/kg/24 h, preferably about 0.001-1 mmol/kg/24 h and more preferably about 0.0001-0.1 mmol/kg/24 h.

Using intravenous administration, the nitrite is preferably administered in a dose within the interval of about 0.01 to about 10000 nmoles/kg body weight/min, preferably about 0.01 to about 1000 nmoles/kg body weight/min, more preferably about 0.1 to about 100 nmoles/kg body weight/min, most preferably about 1 to about 20 nmoles/kg body weight/min. It is presently contemplated that the most preferred dose is less than about 15 nmoles/kg body weight/min. For comparison, it should be noted that the nitrite dose used in the treatment of cyanide poisoning is about 100000 nmoles/kg body weight, or about 300-400 mg given as a single dose. The nitrite can also be administered as one or more bolus doses, preferably 0.01-100 umol/kg body weight, more preferably 0.1-10 umol/kg body weight, and even more preferably 0.1-2 umol/kg body weight.

For the use of a nitrate salt perorally, a dose of about 0.01-100 mmol/kg body weight/24 h is currently preferred or more preferably a dose of about 0.01-10 mmol/kg body weight/24 h, even more preferably 0.1-1 mmol/kg body weight/24 h.

Importantly, the administered dose of nitrate or nitrite should not induce production of more than about 10% methemoglobin, preferably not more than about 5% methemoglobin, and more preferably not more than about 2% methemoglobin. Most preferred is that the dose of nitrate or nitrite does not induce any measurable change in methemoglobin in the subject when administered or ingested according to the prescribed dose.

Pharmaceutically acceptable salts of nitrate and nitrite include but are not limited to sodium, potassium, calcium, zinc, arginine and ammonium. Sodium and potassium salts are presently most preferred.

The nitrite and nitrate salts may be of synthetic origin, but may also be isolated from natural sources, such as naturally nitrate containing plants, e.g. green leafy vegetables, examples include, but are not limited to spinach, lettuce, fennel, cabbage, Chinese cabbage and beetroot. Concentrates, such as juices or dried concentrates of these and other nitrate-rich vegetables or fruits are suitably used for the manufacture of food products (including functional food products) or nutritional supplements according to the present invention. In one preferred embodiment, the nitrate in the inventive composition originates from beetroot (such as beetroot juice). In yet another embodiment of the present invention a nitrate and/or nitrite salt (for example potassium the natural nitrate source includes a dried vegetable powder. In some aspects, the dried vegetable powder is used in combination with licorice, for example salty licorice (ammonium chloride).

Alternatively, the composition comprising nitrite and/or nitrate is a nutritional supplement, an enteral nutritional solution, an infant formula, a snack product or a parenteral nutritional solution comprising inorganic nitrite and/or nitrate in an amount which is sufficient to decrease oxygen consumption, but which does not cause significant hypotension in a subject when ingested by said subject in a prescribed dose.

The inventive composition preferably has the form of a liquid, a paste, a bar, a cake, a powder, a granulate, an effervescent tablet, a chewing gum, a tablet, a capsule, a lozenge, a fast melting tablet or wafer, a sublingual tablet or a spray. Another composition is a nicotine-free smokeless tobacco and/or wet snuff. Such products can be manufactured using conventional methods practiced in the food and beverage industry, or in pharmaceutical industry. More preferably said composition is in the form of, or constitutes a part of, a food product, such as a liquid, a paste, a bar, a cake, a powder, or a granulate.

According to a preferred embodiment, the composition according to the invention is prepared as a fermented food product, such as a yogurt or similar dairy or non-dairy product, comprising a source of nitrate and/or nitrite in addition to live bacteria capable of enhancing nitrate or nitrite reduction.

According to another embodiment, the composition is presented to the market as a functional food product.

The present inventors consider presenting the composition to the market in the form of a sport drink, an energy drink, a sport bar, or an energy bar. The energy bar may take on a variety of forms. For convenience, it is preferred that the energy food product be shaped like a box, square, cylinder, string, pie, sphere, triangle, or other format suitable for packaging, transportation, handling and eating. For example, an energy bar according to the present invention may include, in addition to nitrate and optionally nitrite, also a variety of other components such as, for example, nuts, crisps, fruit pieces, chocolate, seeds, and the like. Preferred nuts are almonds, peanuts, hazelnuts, cashews, walnuts, pecans, brazil nuts, and the like. Crisp components include rice crisps, corn crisps, oats, wheat flakes, and the like. The chocolate can be any type of chocolate or chocolate like edible component in various forms, such as, for example, chocolate chips, chunks, flakes and the like. Non-limiting examples of seeds include sesame, sunflower, poppy, caraway, fennel and the like.

Products comprising the inventive composition can easily be manufactured by persons skilled in the food, sweets and beverage industry or the pharmaceutical industry, and existing compositions supplemented with nitrate, nitrite and other combinations described herein in amounts according to this invention.

Additionally, traditional food ingredients such as flavors and the like may be included. For example, additional ingredients may include natural and artificial flavors, sweeteners, salt, flavor enhancers, color additives, emulsifiers, stabilizers, fats, preservatives, and the like.

In one embodiment of the present invention inorganic nitrite and/or nitrate is administered or used in combination with a polyphenol rich compound or product. Polyphenols are a group of chemical substances found in plants, characterized by the presence of more than one phenol group per molecule. Polyphenols are generally further subdivided into hydrolysable tannins, which are gallic acid esters of glucose and other sugars; and phenylpropanoids, such as lignins, flavonoids, and condensed tannins. In one embodiment of the present invention the inorganic nitrite and/or nitrate is/are mixed with a compound that contains high levels of polyphenols. It is contemplated that this combination will have synergistic health promoting effects via potentiation of NO bioavailability. In some aspects, the combination of nitrite/nitrate and polyphenol rich compound or product will act synergistically to enhance NO formation in the body at the expense of detrimental compounds such as nitrosamines. The beneficial effects of this includes a reduction in blood pressure and platelet aggregation, reduced atherosclerosis, reduced risk of myocardial infarction, stroke and other cardiovascular disorders, reduced risk of cancer in any form. Polyphenols will enhance NO generation by several separate mechanisms highlighted in FIG. 1. First, such agents can directly stimulate endogenous NO formation from NO synthase enzymes (1 in FIG. 1). Second, it is contemplated that these compounds will enhance the reduction of nitrite to bioactive NO due to the presence of reductive —OH groups on the phenol ring (2 in FIG. 1). Third, by acting as scavengers of free radicals such as superoxide, they prevent these radicals from interacting with (and destroying) NO and thereby, NO becomes more long-lived (3 in FIG. 1). In addition to this, nitrite or its reaction products can interact with the polyphenol itself and modify it chemically via nitration or nitrosation reactions ($4a$ in FIG. 1). The resulting compound can act as a long-lived NO donor ($4b$ in FIG. 1). An additional effect is that the presence of polyphenols will divert the chemical reactions away from formation of potentially carcinogenic nitrosamines (5 in FIG. 1). Nitrates reaction product nitrite can react with amines to form nitrosamines but polyphenols will inhibit this reaction by a dual mechanism. First, they help to rapidly reduce $HNO_2$ directly to NO thereby minimizing the formation of nitrosating species ($N_2O_3$, $HNO_2$). Second, they can directly compete for nitrosation with the amines by being nitrosated themselves.

The use of nitrite and/or nitrate or a combination of nitrate and/or nitrite with polyphenols may also have beneficial effects on the blood pressure. Thus, in one embodiment the present invention relates to a method to reduce blood pressure, preferably to normal levels (about 140/80 mmHg). Examples of nitrite and/or nitrate sources are natural sources of nitrate (such as vegetables as mentioned above or juices thereof) or salts of nitrite and/or nitrate. In one particular embodiment beetroot or a juice thereof is administered in order to reduce the blood pressure in a mammal.

The ratio of nitrite/nitrate comprising composition to polyphenol-rich compound should be chosen to obtain enough supply of nitrate. The nitrite/nitrate comprising composition should therefore be at least about 10%, preferably at least about 20%, more preferably at least about 30%, even more preferably at least about 40% and most preferably at least about 50% or even more. Examples of polyphenol rich fruit or juices thereof include, but are not limited to, apple, pear, grapes, lemon, orange, lime, peach, pomegranate, grapefruit, kiwi, ginger and pineapple. Juice from berries are also usable including blackberries, black raspberries, blueberries, cranberries, red raspberries, cherries, bog wortleberry, lingonberries, black elderberry, black chokeberry, black currant, cloudberries and strawberries. Other natural sources of polyphenols include vegetables such as carrots, chili, rhubarb, and onions. In addition, cacao products (rich in flavanols), green or black tea, nuts, Yerba mate and coffee are rich in polyphenols.

In one preferred embodiment, the nitrate in the inventive composition originates from beetroot (such as beetroot juice), which is blended with one or several polyphenol-rich products. The ratio of beetroot juice to polyphenol-rich compound should be chosen to obtain enough supply of nitrate and therefore the beetroot juice part should be at least about 10%, preferably at least about 20%, more preferably at least about 30%, even more preferably at least about 40% and most preferably at least about 50%.

According to one embodiment of the present invention the dose of nitrite and/or nitrate or nitrite and/or nitrate together with polyphenols is administered or manufactured as a chewing gum, lozenge or pastille, wafer, cake, bar or the like which optionally also comprises live non-pathogenic bacteria or some other microorganism. These microorganisms may also be included in "dry form" for example in tablets, capsules, bars, and alike. It can also be administered or manufactured as a functional food product or as a part of a functional food product.

Licorice is well known for its blood pressure elevating effects and it is contemplated that the addition of nitrate/nitrite alone or in combination with a polyphenol will counteract this via the NO-mediated blood pressure lowering effect of these compounds. In particular a salt such as potassium nitrate, sodium nitrate or ammonium nitrate may be used to replace in part or in whole the salt content (such as sodium chloride or ammonium chloride) of the licorice product.

The purpose with the combination with non-pathogenic live bacteria (e.g. the "probiotic" nitrate reducing bacteria) is to further enhance the generation of bioactive compounds such as NO, nitroso adducts or chemically related compounds. This enhancement will occur locally in the gastrointestinal (GI) tract via bacteria-dependent reduction of nitrate and nitrite to NO and other bioactive nitrogen oxides. In particular, this combination will be effective in treating and preventing GI disorders such as ulcers in the stomach, duodenum, jejunum, caecum and colon/rectum. Also, it is contemplated that this combined product will be effective in treating and preventing inflammatory bowel disorders including ulcerative colitis, Crohn's disease, microscopic colitis and other forms. Irritable bowel disease (IBS) is another condition that could be treated with said product. In addition, the compounds formed can be absorbed systemically and have sustained biological effects for example in reducing blood pressure and in preventing atherosclerosis, cancer or any other effect related to enhance NO release as discussed above. The composition with added bacteria can be in the form of a drink such as a juice, yoghurt, a milk-based drink or any other fermented food product. The composition with added bacteria can also be included in different types of functional food. Suitable bacteria are the so called probiotic bacteria, included but not limited to Lactobacilli (for example, *L. acidophilus, L. delbrueckii, L. helveticus, L. salivarius, L. casei, L. curvatus, L. plantarum, L. sakei, L. brevis, L. buchneri, L. fermentum, L. reuteri*) and Bifidobacteria species (for example, but not limited to, *B. breve, B. bifidum*, and *B. lactis*). Other suitable non-pathogenic bacteria that enhance nitrate reduction or nitrite reduction include e.g. *Veillonella* species, *Staphylococcus* species, *Actinomyces* species, or *Rothia* species. The microorganisms to be added to the composition may also be probiotic yeasts (such a *Saccharomyces boulardii*).

In one embodiment, a low concentration of ethanol is added to the inorganic nitrite and/or nitrate composition. In one embodiment ethanol is used in combination with or administered together with the inorganic nitrite and/or nitrate composition. It has surprisingly been found that ethanol even in very low concentrations can generate the potent vasodilator ethyl nitrite following reaction with physiological amounts of nitrite. The reaction is enhanced at acidic conditions such as in the gastric lumen. It is contemplated that ingestion of nitrate will lead to accumulation of nitrite in the saliva and the nitrite will react with ethanol in the stomach thereby forming ethyl nitrite. For example, if the inventive composition is in the form of a liquid the ethanol content should be below about 5% (v/v), more preferably below about 2% (v/v), and most preferable between about 0.5-1.5% (v/v).

In one embodiment of the present invention a cacao product such as dark chocolate that is rich in flavanols is combined with a nitrate-rich natural compound in a drink or a chocolate bar. One preferred nitrate-rich compound in this embodiment is rhubarb. Again, the nitrate will potentiate the effect of the flavanols via enhancement of NO formation as described above and in FIG. 1.

Contamination of a nitrate-containing food or drink with unwanted bacteria may result in a large accumulation of nitrite, due to nitrate reducing bacterial enzymes. Ingestion of high levels of nitrite may cause potentially serious methemoglobinemia. In one embodiment, a nitrate-rich composition is mixed with a compound that inhibits unwanted bacterial growth. Such compound should be chosen so as not to affect the taste of the product negatively. Ideally, it should enhance the taste and at the same time increase the bioactivity of the product. One option is to acidify the inventive composition so that final pH is below about 5, and most preferably between about pH 2-4. This will inhibit and/or abolish bacterial growth. Suitable acidifying agents can be any agent that reduces pH and include artificial compounds as well as natural juices from e.g., but not limited to, lemon or lime, ascorbic acid, acetic acid or vinegar (from apple, grapes or other fruits). It is contemplated that with the use of natural products a dual effect is achieved. Besides having an antibacterial effect, they are rich in polyphenols, which enhance the generation of bioactive NO from nitrate/nitrite in the vegetable drink. In one particular embodiment, a nitrate-rich vegetable juice (e.g. beetroot juice) is mixed with a compound that inhibits undesirable bacterial growth.

According to an embodiment of the invention, the nitrate and nitrite salts are combined with other pharmaceuticals including but not limited to: anti-diabetic drugs (insulin and oral anti-diabetics), cardiovascular drugs (statins, ACE inhibitors, beta-receptor antagonists, diuretics, angiotensin 2 receptor antagonists, organic nitrates, calcium channel blockers) acid secretion-inhibitors (proton pump inhibitors, Histamine-2 receptor blockers), oral anti-diabetics including biguanides, sulphonureides, alpha-glucosidase inhibitors, thiazolidinediones, glinides; drugs for treatment of pulmonary hypertension including prostacyclin analogues, endothelin receptor antagonists and sildenafil.

According to one embodiment the nitrite is delivered systemically via peroral treatment with an organic nitrate including nitroglycerine or isosorbide mono/di-nitrate. Nitroglycerine is used clinically to treat angina pectoris and it acts by releasing vasodilatory nitric oxide systemically. However, this drug must be given parenterally because the first passage metabolism in the liver is considerable. Interestingly, it has been found that the liver metabolism of nitroglycerine yields predominantly nitrite. Considering the novel biological effects of nitrite described here, nitroglycerine may therefore be used as a "prodrug" of nitrite. Preferably the drug should then be given by the enteral route (with liver metabolism) to maximize nitrite generation while at the same time avoiding the acute vasodilatation and drop in systemic blood pressure associated with iv or sublingual administration of nitroglycerine. A suitable dose range when giving nitroglycerine perorally is about 0.001 to 10 mol/kg/24 hours, preferably about 0.001 to 1 mol/kg/24 hours, more preferably 0.01 to about 0.1 mmol/kg/24 hours. The tablets should preferably be coated to avoid absorption in the oral cavity.

According to one embodiment nitrite and/or nitrate is added to parenteral and enteral feeding/nutrition solutions to be used in adults, children, neonates and prematures. Today such solutions are generally extremely low in nitrate and nitrite as noted in measurements performed by the present inventors (not shown). An intubated mechanically ventilated patient with parenteral nutrition is particularly deprived of nitrate/nitrite. First, these patients do not produce and swallow saliva properly and thus one great nitrate/nitrite source is disrupted. Secondly as stated above, the feeding they receive contains almost no nitrate/nitrite. Many intensive care patients suffer from metabolic disturbances, in particular catabolism due to stress and trauma and their metabolic rate is often increased. Moreover, insulin resistance is common and glucose homeostasis is disturbed. Tight control of plasma glucose by administering insulin is advocated in these patients. Also, healthy subjects, such as infants or subjects taking enteral solutions for other reasons can benefit from the compositions and methods of the present invention. Enteral nutrition is thus meant to include also infant formulas and other enteral products.

When given preoperatively, the amount of carbohydrates in the drink will provide the patient with preferably about 200 kcal, more preferably about 100 kcal and most preferably about 50 kcal. For the use of a nitrate salt perorally, a dose of about 0.01-100 mmol/kg body weight/24 h is currently preferred or more preferably a dose of about 0.01-10 mmol/kg body weight/24 h, even more preferably 0.1-1 mmol/kg body weight/24 h.

Using intravenous administration pre- and/or peroperatively, the nitrite is preferably administered in a dose within the interval of about 0.01 to about 10 000 nmoles/kg body weight/min, preferably about 0.01 to about 1000 nmoles/kg body weight/min, more preferably about 0.1 to about 100 nmoles/kg body weight/min, most preferably about 1 to about 20 nmoles/kg body weight/min. It is presently contemplated that the most preferred dose is less than about 15 nmoles/kg body weight/min.

Therapeutic Methods of Use

In one embodiment, provided herein are uses of nitrites and/or nitrates, for the manufacture of pharmaceutical products, enteral or parenteral nutritional solutions, preoperative compositions, nutritional supplements, or functional food products for administration to both healthy persons, such as athletes, or to patients, suffering from one or more of the conditions exemplified herein. Included in this embodiment are also possible combinations of nitrites and/or nitrates with other compounds as mentioned above.

In one embodiment, provided herein are methods for the treatment, alleviation and/or prevention of clinical conditions, comprising administering an effective amount of a nitrate and/or a nitrite to a patient in need thereof sufficient to treat, alleviate and/or prevent such condition.

There are many possible clinical conditions where such treatment, alleviation and/or prevention is performed using nitrate and/or nitrite according to the present invention:

glucose control in diabetes/prediabetes metabolic syndrome

The method and composition according to the invention also has general therapeutic, alleviating and/or prophylactic effects in patients under metabolic stress. Examples include but are not limited to:

intensive care patients patients undergoing surgery patients suffering from malnutrition of different genesis cancer with anorexia burn injury trauma neonates/prematures anorexia nervosa thyroid disorders (e.g. hyperthyreosis/hyperthyroidism)

myocardial infarction, cardiac arrest major systemic disease with a catabolic state stress ulcers (gastric)

surgical gut anastomosis insufficiency fever myocardial infarction and cardiac arrest ischemia-reperfusion injury (MI, stroke, arterial insufficiency or any other organ ischemia)

sleep apnea syndrome septic chock insufficient perfusion of the intestines

Patients treated in the ICU (intensive care unit) are often subjected to severe metabolic stress due to trauma, infection, pain and other pathological processes. Such patients are treated for several reasons including but not limited to post-surgical observation, trauma, bleeding, burn injury, brain injury, stroke, diabetes, sepsis, septic shock, myocardial infarction, cardiac arrest, arterial insufficiency or any other organ ischemia, chronic obstructive pulmonary disease, asthma and other severe inflammatory conditions, pulmonary hypertension, congestive heart failure, pulmonary embolism. This results in varying degrees of catabolism and resistance to insulin with a disturbed glucose handling. They also often suffer from vascular endothelial dysfunction leading to microcirculatory disturbances. As mentioned above these patients are given only minute amounts of nitrate/nitrite in the enteral and parenteral feeding and due to several reasons (sedation, intubation) they have a disturbed enterosalivary circulation of nitrate/nitrite compared to healthy people.

It is contemplated that addition of sufficient amounts of nitrite and/or nitrate in the parenteral and/or enteral feeding to patients treated in the intensive care unit, may alleviate or prevent the aforementioned metabolic and circulatory disturbances by decreasing the rate of metabolism, enhancing blood glucose homeostasis and microcirculatory improvement.

Patients undergoing surgery are subjected to a varying degree of surgical trauma. This triggers catabolic hormones like cortisol, glucagon and adrenalin and such patients may develop transient insulin resistance. Common clinical procedure involves fasting in order to reduce gastric content, which could be accidentally aspirated in the airways if the patient vomits or regurgitates during anesthesia. Such fasting eliminates the intake of nitrate/nitrite and it has been shown that systemic levels of nitrate and nitrite are reduced after fasting. It is contemplated that administration of nitrite and/or nitrate pre, per or postoperatively will improve the metabolic situation (decreasing the rate of metabolism, enhancing blood glucose homeostasis) in surgical patients. Moreover, during the entire perioperative period the patients are at higher risk for ischemic events due to hypotension, hypoxia and microcirculatory disturbances. Such events will initiate ischemia-reperfusion processes, which may injure several organ systems within the body. It is contemplated that prophylactic administration of nitrite and/or nitrate, either as a preoperative drink containing nitrate and/or nitrite anions, a suitable vegetable juice such as but not limited to beetroot juice or by giving nitrate and/or nitrite via the parenteral route, will reduce the negative effects of ischemia-reperfusion events during surgery in several organs including but not limited to brain, heart, lung, liver, kidney and skeletal muscle.

Ischemia-reperfusion injury during myocardial infarction is a major problem in clinical care. State-of-the art treatment of myocardial infarction includes reopening of occluded coronary vessels by pharmacological means with thrombolytic agents and/or percutaneous coronary intervention. It is considered that the method and composition according to the invention will reduce ischemia-reperfusion injury by increasing blood flow and by altering mitochondrial function. From experiments in the present application it is also considered that during ischemia-reperfusion nitrate and nitrite could reduce oxygen consumption possibly by a "hibernating" effect on mitochondria. Another mechanism by which nitrate and nitrite could ameliorate ischemia-reperfusion injury is by reducing oxygen radical formation and cytochrome C release from the mitochondria. The effect of nitrate and nitrite on mitochondrial function is most likely mediated by nitric oxide (NO) interacting with oxidative phosphorylation and/or s-nitrosylation of protein complexes in the mitochondrial respiratory chain. It is envisaged that the time point for administration of nitrate and/or nitrite in relation to the myocardial infarction induced ischemia-reperfusion injury will be effective both pre, per or post injury. Both a pre- and post-conditioning effect of nitrate and/or nitrite is considered which means that a patient can receive treatment already in the ambulance on his/her way to the hospital, at the hospital before and after reperfusion of the coronary circulation and also at the ward. Also, patients at high risk of developing a myocardial infarction (e.g. angina pectoris, congestive heart failure) could be considered for prophylactic treatment with the method and composition according to the invention. After cardiac arrest and resuscitation systemic ischemia-reperfusion injury develops involving several major organ systems, including the brain. It is contemplated that nitrate and/or nitrite is beneficial both given prophylactic to patients with high risk for cardiac arrest and also during resuscitation procedures.

According to a preferred embodiment, the nitrate and/or nitrite or any combination mentioned herein is/are also given pre-operatively to patients scheduled to undergo surgery or substantive, invasive examination procedures. In one particular embodiment, inorganic nitrite and/or nitrate are combined with carbohydrates. Thus, such combinations include, but are not limited to nitrate alone; nitrate and nitrite; nitrate, nitrite, and carbohydrates; nitrate and carbohydrates; nitrite alone and nitrite and carbohydrates. In addition, polyphenols may be added to any of the aforementioned combinations. Any such combination can be administered (in single or repeated doses) as a preoperative drink or the like prior to surgery or intravenously prior or during surgery. An appropriate time to administer such a preoperative drink is between 72 and 2 hours before surgery. A combination of nitrite and/or nitrate with carbohydrates may ameliorate insulin resistance and also ischemia/reperfusion injury common in the preoperative and postoperative period. Examples of carbohydrates include but are not limited to glucose, fructose, maltodextrin, sucrose, lactose, galactose and mannose.

In patients suffering from arterial insufficiency, including but not limited to intermittent claudication, pharmacological treatment aims at improving blood flow in the affected limb(s) and to stimulate angiogenesis to promote new vessel formation. Phosphodiesterase inhibitors and growth factors have been studied in clinical trials but results are variable. Likewise, studies with traditional NO donors such as organic nitrates have been less successful. It is contemplated that the method and composition according to the invention will positively stimulate both blood flow and angiogenesis thereby improving the condition in these patients. Treatment with nitrate/nitrite is attractive since it will preferentially increase blood flow in the ischemic areas without causing troublesome systemic effects such as hypotension, which is a risk when using organic nitrates that dilate non-selectively in most vascular beds. In addition, nitrite will affect mitochondrial function as discussed above resulting in less oxygen demand in the ischemic tissue.

In patients suffering from malnutrition, including but not limited to cancer with anorexia, anorexia nervosa, gastrointestinal disease, it is contemplated that the method and composition according to the invention will have an anabolic effect and will reduce oxygen consumption. It is contemplated that this effect is achieved by improving mitochondrial efficiency and attenuating mitochondrial uncoupling.

The method and composition according to the invention also has general therapeutic effects in patients with erectile dysfunction. In this condition, the endogenous NO system is failing. Administration of nitrite and/or nitrate (and possible combinations outlined above) will enhance NO formation locally in the corpus cavernosum, thereby enhancing erection.

It is contemplated that the method and composition according to the invention has general therapeutic, alleviating and/or prophylactic effects in patients with gastritis and gastric ulcers due to *Helicobacter pylori* infection, stress or side effects from pharmacological treatment such as the use of Non-Steroidal Anti-Inflammatory Drugs (NSAID). By improving gastric mucosal blood flow, mucus generation and by anti-bacterial and anti-inflammatory properties the method and composition will have beneficial effects in these patients. In addition, unwanted side effects of treatment with acetylsalicylic acid, NSAIDs or any other ulcerogenic drug in other parts of the gastrointestinal tract (duodenum, small and large intestines) are prevented by said method and composition.

A feared problem in surgery is gut anastomosis insufficiency and insufficient perfusion of the intestines. New methods for improving microcirculation in the anastomosis are constantly investigated. It is contemplated that the method and composition according to the invention will improve microcirculation in the anastomosis, which will enhance the healing process. It is also considered that the invention will improve circulation in situations with insufficient perfusion of the intestines.

Patients with sleep apnea syndrome are at higher risk for developing hypertension and other cardiovascular diseases. Moreover, they are subjected to periods of hypoxia during sleep. It is contemplated that the method and composition according to the invention will protect against hypoxia-induced injury by improving circulation and by reducing oxygen consumption possibly by a "hibernating" effect on mitochondria. Other mechanism by which said method and composition could have protective effects is by reducing oxygen radical formation and cytochrome C release from the mitochondria. The effect of nitrate and nitrite on mitochondrial function is most likely mediated by nitric oxide (NO) interacting with oxidative phosphorylation and/or s-nitrosylation of complexes in the mitochondrial respiratory chain.

The method and composition according to the invention has general therapeutic, alleviating and/or prophylactic effects also in patients with pathological conditions characterized by low oxygen availability, including but not limited to chronic obstructive airway disease (COPD), inflammatory airway disease such as asthma, pulmonary hypertension, congestive heart disease, interstitial lung disease, pulmonary embolism, ischemic heart disease, peripheral artery disease, sleep apnea syndrome, myocardial infarction and systemic inflammatory disorders. In these conditions, addition of oxygen promptly improves arterial oxygenation and total body oxygen delivery. For technical and safety reasons, it is complicated to administer oxygen outside hospital facilities. Another way to improve the situation for these patients is to reduce the need for oxygen. The method and composition according to the invention lead to reduced oxygen cost in relation to the physical work performed. This highly surprising finding is especially relevant in the patients with the aforementioned conditions since oxygen availability is the limiting factor for physical activity. It is envisaged that the method and composition according to the invention will facilitate physical activity in these patient groups.

In one preferred embodiment nitrate and/or nitrite is given to patients with a pathological condition characterized by low oxygen availability. In such situations, it is desirable to reduce the tissues need for oxygen to prevent sequel and symptoms associated with the hypoxia. Examples include patients with COPD whose pulmonary oxygen uptake may be severely compromised and patients with peripheral artery disease where oxygen delivery to the tissues is reduced.

Non-Therapeutic Effects and Methods of Use

The inventive method and composition is also useful for healthy subjects, e.g. athletes. The inventive method and composition provides for less oxygen demand at a certain workload and improves anabolism. The method and composition is also useful for oxygen sparing at high altitude, for example in work and sports performed in a low oxygen environment, such as but not limited to rescue activities, firefighting, military operations, diving, mountain climbing, high-altitude flying, and the exploration of space.

The present method and composition is also useful in solid organ or tissue transplantation, in order to minimize metabolic demand of the donated organ before transplantation, and to improve survival of the transplanted organ or tissue after transplantation. Nitrite and/or nitrate or any combination mentioned herein is/are given either into the organ or tissue by perfusion, topically on the organ or tissue and/or systemically to the donor before transplantation, and into the organ or tissue by perfusion or topically on the organ or tissue and/or systemically to the receiver after transplantation.

In one preferred embodiment nitrate and/or nitrite is/are or any combination mentioned herein given to patients that are at risk of developing significant metabolic stress. Such situations include many of the conditions listed above including surgical stress and trauma. Oxygen demand and consumption increases dramatically during stress. Thus, an improved situation is achieved by decreasing the oxygen demand in these patients. According to one preferred embodiment nitrate and/or nitrite is given to patients to prevent the sequel associated with physiologic or traumatic stress. Examples include patients that come into the emergency room after trauma or patients undergoing major surgery.

To the best of the knowledge of the inventors, this is the first study to examine the effects of dietary nitrate on the cardiopulmonary and metabolic response to exercise. The main finding was that dietary supplementation with inorganic nitrate, in an amount which does not cause significant hypotension and without any significant increase in methemoglobin and plasma lactate, results in a reduced $VO_2$ during submaximal work and a significant increase in muscular efficiency. These effects occurred without any changes in $VO_2$peak values or maximal attainable work rate. Thus, the present invention also makes available a second nonmedical use of inorganic nitrate and/or nitrite, i.e. for the manufacture of a composition for enhancing the performance of a mammal wherein the effect of enhancing performance is manifested as reduced $VO_2$ during physical exercise. Preferably the effect of enhancing performance is manifested as both a reduced $VO_2$ during physical exercise and a significant increase in muscular efficiency.

Accordingly, in one implementation, the inventors make available a method for non-therapeutically enhancing the performance of a mammal, wherein inorganic nitrate and/or nitrite is administered to said mammal. Said mammal is chosen among a human, a horse, or a dog, preferably a human.

According to one particular embodiment, only nitrite is administered.

Without wishing to be bound by theory, the inventors consider that there is reason to believe that the observed effects involve initial reduction of nitrate to nitrite. Nitrate itself is believed to be biologically inert and cannot be metabolized by mammalian cells. However, after ingestion nitrate re-enters into the mouth via the salivary glands and is effectively reduced by commensal bacteria thereby forming nitrite. In contrast to nitrate the nitrite ion has recently been shown to possess a wide range of bioactivities. In the present study, the inventors did indeed note an increase in plasma nitrite after the nitrate treatment period thereby confirming in vivo reduction of nitrate as described previously. Another finding in support of nitrite being bioactive was its effective consumption during exercise in contrast to the unchanged levels of plasma nitrate. Ultimately the bioactivity of nitrite is likely related to its further reduction to NO and possibly other closely related nitrogen intermediates. In addition, it has been recently suggested that, nitrite itself may directly affect cellular signaling pathways. Although probably unlikely, at this stage effects of the nitrate ion itself cannot be excluded. There are several principle ways by which biological effects of nitrogen oxides may be propagated including activation of cGMP, alteration of protein function by a nitro(syl)ation/nitration or direct binding to protein heme-moieties of several proteins as in the prototypic activation of guanylyl cyclase by NO. In addition, nitrite itself may also directly affect cellular signaling pathways.

If the effects proceed via nitrate reduction to nitrite and then NO formation, how could this then explain the present results? Earlier studies using NOS inhibitors to block endogenous NO production give some indications. NOS-inhibition has been shown to increase submaximal $VO_2$ in dogs during exercise, independently of the reduction in blood flow. This increase in $VO_2$ during NOS-blockade has been linked to the fact that NO affects tissue respiration in vitro by reversible inhibition of the respiratory enzyme cytochrome c oxidase. Others have related the increased $VO_2$ during NOS-blockade to an inhibiting effect of NO on proton leakage via the mitochondrial permeability transition pore (mPTP) were a considerable amount of protons leak over the inner mitochondrial membrane. If the effects of nitrate were solely due to inhibition of cytochrome c oxidase (thereby inhibiting oxidative phosphorylation) one would expect an increase in anaerobic metabolism during physical exercise and a larger accumulation of lactate. However, judging from the results this was not the case, as the plasma lactate concentration was near identical after nitrate supplementation compared to placebo.

The finding that the oxygen pulse at a given work rate decreases by nitrate supplementation is a direct effect of the lower oxygen demand at that work rate. However, there is no difference in oxygen pulse at a given absolute oxygen uptake. The lack of effect of nitrate on VE/VO$_2$ or oxygen pulse indicates that the improved efficiency originates from muscular or mitochondrial adaptations rather than from central adaptations in the heart or the lungs.

There is reason to believe that the observed effects of nitrate on physical performance involve initial reduction of nitrate to nitrite. Nitrate itself is believed to be biologically inert and cannot be metabolised by mammalian cells. However, after ingestion nitrate re-enters into the mouth via the salivary glands and is effectively reduced by commensal bacteria thereby forming nitrite. In contrast to nitrate the nitrite ion has recently been shown to possess a wide range of bioactivities.

The inventors noted an increase in plasma nitrite after the nitrate treatment period thereby confirming in vivo reduction of nitrate as described previously (Lundberg & Govoni 2004, LARSEN, F J, et al. Effects of dietary nitrate on blood pressure in healthy volunteers. N Engl J Med. 2006, vol. 255, no. 26, p. 2792-3). Another finding in support of nitrite being bioactive was its effective consumption during exercise in contrast to the unchanged levels of plasma nitrate. Ultimately the bioactivity of nitrite is likely related to its further reduction to NO and possibly other closely related nitrogen intermediates. In addition, it has been recently suggested that nitrite itself may directly affect cellular signalling pathways (BRYAN, N S, et al. Nitrite is a signaling molecule and regulator of gene expression in mammalian tissues. Nat Chem Biol. 2006, vol. 1, no. 5, p. 290-7). Although probably unlikely, at this early stage, effects of the nitrate ion itself cannot be excluded. There are several principle ways by which biological effects of nitrogen oxides may be propagated including alteration of protein function by nitrosylation, nitration or direct binding to protein heme-moieties as in the prototypic activation of guanylyl cyclase by NO.

Earlier studies using NOS inhibitors to block endogenous NO production give some indications. NOS-inhibition has been shown to increase submaximal VO$_2$ in dogs during exercise, independently of the reduction in blood flow (SHEN, W. et al. Nitric oxide. An important signaling mechanism between vascular endothelium and parenchymal cells in the regulation of oxygen consumption. Circulation. 15 Dec. 1995, vol. 92, no. 12, p. 3505-12, ISHIBASHI, Y, et al. ATP-sensitive K+-channels, adenosine and NO-mediated mechanisms account for coronary vasodilation during exercise. Circulation Res. 1998, no. 82, p. 346-359; Shen et al. 1999, supra). The increase in VO$_2$ during NOS-blockade has been explained by the fact that NO affects tissue respiration by reversible inhibition of the respiratory enzyme cytochrome c oxidase (Carr & Ferguson 1990, supra; Bolanos et al. 1994, supra; Brown & Cooper 1994, Cleeter et al. 1994, Schweizer & Richter 1994). Others have related the increased VO$_2$ during NOS-blockade to an inhibiting effect of NO on proton leakage over the inner mitochondrial membrane (BOHUSLAVS'KYI, A, et al. Effect of nitric oxide on the efficiency of oxygen consumption by the working skeletal muscle in fatigue. Fiziol Zh. 2005, vol. 51, no. 1, p. 33-42; NAVET, R, et al. Proton leak induced by reactive oxygen species produced during in vitro anoxia/ reoxygenation in rat skeletal muscle mitochondria. J Bioenerg Biomembr. 2006, vol. 38, no. 1, p. 23-32; WANG, G, et al. Nitric oxide donors protect murine myocardium against infarction via modulation of mitochondrial permeability transition. Am J Physiol Heart Circ Physiol. 2005, vol. 288, no. 3, p. 1290-5). If the effects of nitrate were solely due to inhibition of cytochrome c oxidase one would expect an increase in anaerobic metabolism during physical exercise and a larger accumulation of lactate. However, judging from the results this was not the case, as the plasma lactate concentration was near identical after nitrate supplementation compared to placebo. The inventors consider this to be very surprising.

The studies using NOS inhibitors cited above all imply that endogenous NO is involved in regulation of oxygen consumption but there have been few attempts to study the effect of exogenous NO delivery. Studies with NO-donors such as nitroprusside and nitroglycerine have shown somewhat diverging results, with decreases in VO$_2$ in some cases (RECCHIA, F A, et al. Nitric oxide controls cardiac substrate utilization in the conscious dog. Cardiovasc Res. 1999, no. 44, p. 325-32; LOKE, K E, et al. Nitric oxide modulates mitochondrial respiration in failing human heart. Circulation. 21 Sep. 1999, vol. 100, no. 12, p. 1291-7), no effect in one study (NUNEZ, C, et al. Discrepancies between nitroglycerin and NO-releasing drugs on mitochondrial oxygen consumption, vasoactivity, and the release of NO. Circ Res. 11 Nov. 2005, vol. 97, no. 10, p. 1063-9) and increases in other settings (DE BACKER, D, et al. Effects of dobutamine on the relationship between oxygen consumption and delivery in healthy volunteers: comparison with sodium nitroprusside. Clin Sci (Lond). 1996, vol. 90, no. 2, p. 105-11).

Several of the proposed mechanisms for nitrite reduction to NO described above could theoretically come into play during physical exercise. Thus, all these pathways are greatly enhanced during hypoxia and when pH decreases such as in a working muscle. Shiva and colleagues very recently demonstrated deoxymyoglobin-dependent nitrite reduction to NO in rat heart homogenates with a concomitant inhibition of mitochondrial respiration (Shiva et al 2007, supra). Another possible pathway includes NO formation by the mitochondria themselves (KOZLOV, A V, et al. Nitrite reductase activity is a novel function of mammalian mitochondria. FEBS Lett. 2 Jul. 1999, vol. 454, no. 1-2, p. 127-30) or even simple acidic reduction of nitrite in the working muscle (Zweier et al. 1995, supra, MODIN, A, et al. Nitrite-derived nitric oxide: a possible mediator of 'acidic-metabolic' vasodilation. Acta Physiol Scand. 2001, vol. 171, no. 1, p. 9-16). Cosby and colleagues described NO formation and vasodilation from the reaction of circulating nitrite ions with deoxyhemoglobin in blood (COSBY, K, et al. Nitrite reduction to nitric oxide by deoxyhemoglobin vasodilates the human circulation. Nat. Med. 2003, vol. 9, no. 12, p. 1498-505). While this latter pathway, and possibly also tissue nitrite reduction, very well might explain the recently described nitrate-induced reduction in resting blood pressure (Larsen et al. 2006), it is still not obvious how this NO also would decrease oxygen consumption in the working muscle. Thus, an effective inhibition of mitochondrial respiration e.g. by deoxymyoglobin-derived NO, would again be expected to result in accumulation of plasma lactate which was not the case.

The efficiency of the muscles to produce work has been related to the percentage of type I muscle fibres (COYLE, E F, et al. Cycling efficiency is related to the percentage of type I muscle fibers. Med Sci Sports Exerc. 1992, vol. 24, no. 7, p. 782-8) and uncoupling protein-3 (UCP3) content of muscle fibres (MOGENSEN, M, et al. Cycling efficiency in humans is related to low UCP3 content and to type I fibers but not to mitochondrial efficiency. J Physiol. 2006, vol. 571, no. 3, p. 669-681). Other factors that might contribute to the efficiency of movement are anatomical, biochemical and biomechanical features (WILLIAMS, K R. The relationship between mechanical and physiological energy estimates. Med Sci Sports Exerc. 1985, no. 17, p. 317-25). Thus, simply measuring differences in $VO_2$ at different work rates is not an optimal estimate of muscular efficiency because the energy output for a certain $VO_2$ is dependent upon substrate utilization. Gross efficiency (GE) calculations include possible changes in respiratory exchange ratio and thereby take substrate utilization into account. The improved GE after nitrate supplementation indicates better efficiency, but even so, it cannot be excluded that this improved efficiency originates from reduced baseline energy expenditure (EE). The Delta efficiency (DE) calculations are not dependent on the baseline EE and are also based on all work rates taken together instead of a single work rate at a time as in the GE-calculations. It is therefore plausible to expect DE to be the most valid estimate of muscular efficiency in this case. Indeed, even DE was significantly improved after nitrate supplementation. It is unlikely that the improved efficiency by nitrate comes from mechanical factors. The subjects of this study were all cyclists with many years of experience of training and competing. It is improbable that a few visits to the laboratory would change their efficiency during cycling to any noteworthy extent. Especially since the subjects used the same cycling shoes, clip-on pedals and the same seat position as they were used to during training makes this even more unlikely. More important, the randomization procedure used in this study rules out any such differences. Marcheal and Gailly (MARCHEAL, G, et al. Effects of nitric oxide on the contraction of skeletal muscle. Cell Mol Life Sci. 1999, no. 55, p. 1088-1102) demonstrated a faster relaxing velocity of muscle fibres in in situ experiments during administration of an NO-donor, thereby implicating a neuromuscular modulatory effect of NO. It remains to be proven if this can improve the muscular efficiency during cycling.

The finding that the oxygen pulse at a given work rate decreases by nitrate supplementation is a direct effect of the lower oxygen demand at that work rate. However, there is no difference in oxygen pulse at a given absolute oxygen uptake. The lack of effect of nitrate on $VE/VO_2$ or oxygen pulse indicates that the improved efficiency originates from muscular or mitochondrial adaptations rather than from central adaptations in the heart or the lungs.

In summary, the present findings demonstrate a lower oxygen cost during submaximal work after dietary supplementation with nitrate, in amounts achievable through the intake of a non-toxic amount of nitrite. This occurred without an accompanying increase in plasma lactate, indicating that the energy production had become more efficient. The mechanism of action and main targets need to be clarified but the process likely involves in vivo reduction of nitrate into bioactive nitrogen oxides including nitrite and NO.

Examples

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

The present inventors have been studying the effects of nitrate and nitrite on various physiological functions including blood pressure, glucose metabolism and energy expenditure in vivo. In the examples below, unless otherwise noted, nitrate was administered perorally and nitrite was administered intravenously (iv). Oxygen consumption was measured using indirect calorimetry.

1. Intravenous Sodium Nitrite and Resting Energy Expenditure

Figure 2:
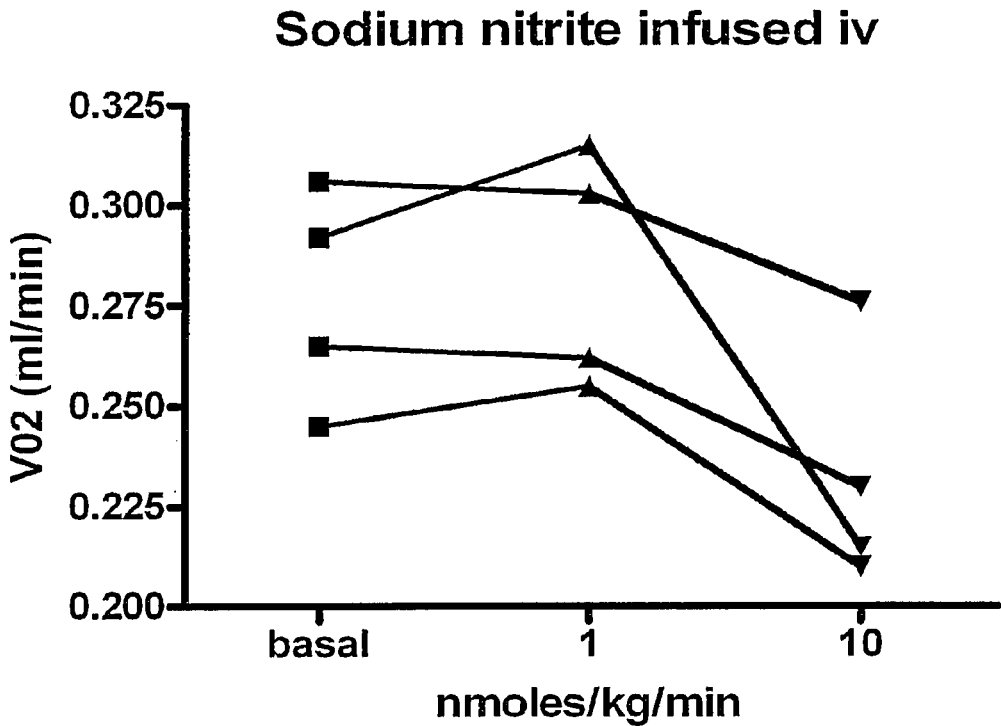
FIG. 2 is a graph showing changes in oxygen consumption ($VO_2$) following iv infusion of sodium nitrite in increasing doses. Nitrite was infused over a 10 min period in non-smoking healthy male volunteers (30-70 years).
Figure 3:
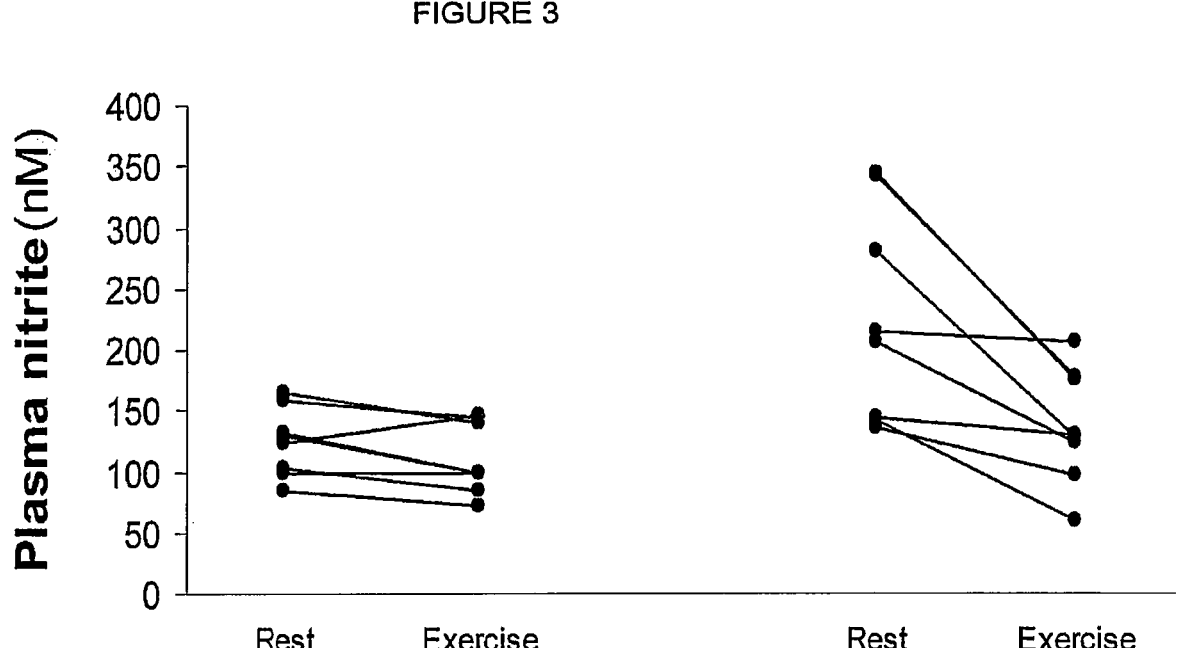
FIG. 3 is a graph showing the effects of a dietary supplementation with sodium nitrate or sodium chloride (placebo) on plasma concentrations of nitrite measured at rest and immediately after exercise in 9 healthy male volunteers.
Figure 4:
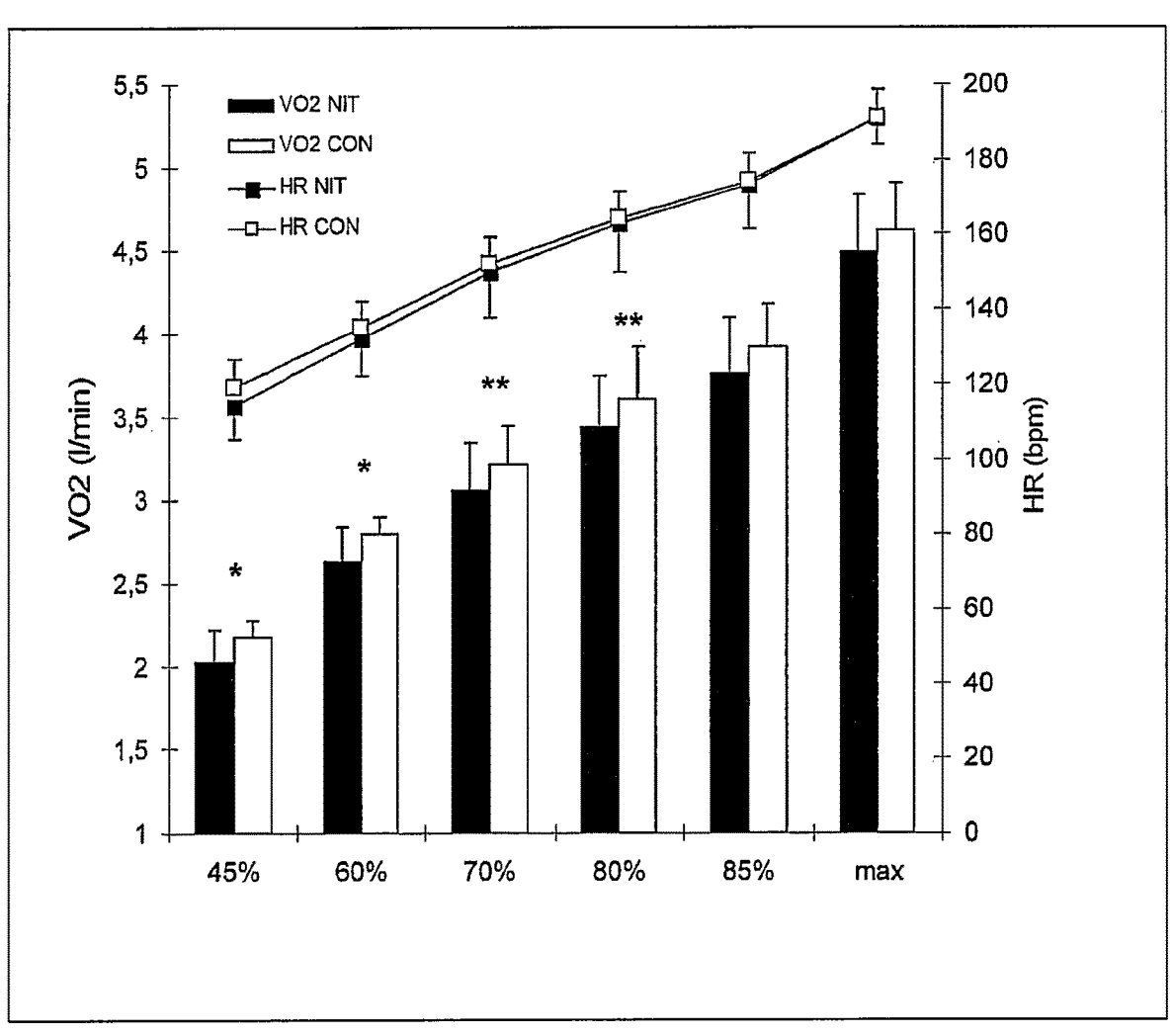
FIG. 4 is a bar diagram showing the oxygen consumption ($VO_2$) and heart rate (HR) measured at 6 different work rates after a 3-day dietary supplementation with sodium nitrate (0.1 mmol/kg body weight/min, NIT) or an equal amount of sodium chloride (CON). The study had a randomized double-blind cross-over design with a washout period of at least 10 days between the tests. * $p<0.05$, ** $p<0.01$.

Resting energy expenditure (as measured by indirect calorimetry) is reduced by 10-25% after 10 min of iv infusion of sodium nitrite (n=4, FIG. 3). Prior to the test the subjects had been on a diet low in nitrate for one day and had been fasting for at least 8 h. The major drop in energy expenditure was seen when infusing nitrite at a concentration of 10 nmoles/kg body weight/min during 10 minutes. At 1 nmol/kg body weight/min no obvious effects were noted during the 10 min observation period and after 100 nmol/kg body weight/min no further decrease in oxygen consumption was noted as compared to the 10 nmol dose. In separate experiments (n=2) the present inventors noted an increase in plasma nitrite from 140-165 nM to 370-480 nM after the 10 nmol/kg body weight/min infusion (10 min infusion). Basal levels of methemoglobin were 1.1-1.3 mmol/1 and did not change significantly after infusion of nitrite (1.1-1.4 mmol/1) See FIG. 2.

2. Oral Sodium Nitrate and Oxygen Consumption During Exercise

A. Methods

Subjects: Nine healthy, well trained ($VO_2$peak 55±3.7 ml×kg$^{-1}$×min$^{-1}$), males (28±6 years) volunteered for the study. All subjects were trained cyclists or triathletes and well accustomed to the testing procedure. It was chosen to use well-trained subjects to avoid training effects from the tests such as enhanced $VO_2$peak or better mechanical efficiency during submaximal exercise. The protocol was approved by the regional ethics committee in Stockholm and all subjects gave their written consent prior to participation.

Dietary supplementation with nitrate: The aim with the present study was to investigate the effects of two distinct dietary patterns, one with higher, and one with lower than normal nitrate intake. The study had a double-blind placebo-controlled crossover design. During two three-day periods, separated by a washout interval of ten days, the subjects were instructed to avoid all foods with moderate or high nitrate content (all vegetables, all cured meats, strawberries, grapes, and tea). In addition, they were told to restrain from alcohol and tobacco products. Otherwise they were free to eat any food they liked during the three days of restricted diet. The subjects were randomized to start with either ingestion of 0.1 mmol sodium nitrate/kg body weight/day dissolved in water or an equal amount of sodium chloride (placebo). The daily dose was divided and ingested three times daily. The different solutions could not be distinguished by taste or appearance. The daily nitrate dose corresponded to the amount normally found in 150-250 gram of a nitrate-rich vegetable such as spinach, lettuce or beetroot. The last dose of nitrate or placebo was ingested in the morning on the day of measurement (see the main tests below). The order between the nitrate supplementation period (NIT) and the placebo period (CON) was balanced. During the washout period the subjects did not adhere to any specific dietary regime.

Experimental protocol: Measurements were carried out on an electrically braked cycle ergometer (Monark 839E, Varberg, Sweden) that was modified with a racing saddle and the pedal system the subjects were familiar with from training. The bicycle ergometer was computer-controlled, permitting a constant work rate regardless of the cadence the subject chose to pedal with. The pedaling cadence was individually chosen in the range of 70-90 rpm but kept constant during the test to minimize differences in work output due to changes in muscle recruitment patterns.

Pulmonary ventilation ($V_E$), oxygen uptake ($VO_2$), $CO_2$ output ($VCO_2$) and respiratory exchange ratio (RER) were measured at 10 second intervals by a computerized gas analyzer (AMIS 2001, Odense, Denmark) connected to a flow meter which the subjects breathed through via a mouthpiece and a plastic tube. Heart rate (HR) was continuously recorded during the tests with a portable heart rate monitor (Polar S610, Polar, Kempele, Finland). Capillary blood samples (20 μl) were collected from the fingertip and were analyzed for lactate ([Hla]) using a Biosen C-Line Sport Analyser (EKF diagnostics, Magdeburg, Germany). Haemoglobin concentration ([Hb]) at rest was determined with capillary blood taken from the fingertip and analyzed with an Hb-measuring device (Hemocue, Angelholm, Sweden). Hematocrit (Hct) was determined by centrifuging capillary blood at 12000 rpm for three minutes.

Pre-tests: Each subject attended the laboratory twice within a two-week period before the first main tests. The first pre-test was carried out to familiarize the subject with the bicycle ergometer and the testing procedure. The subjects did a preliminary test at five submaximal levels with every level lasting for five minutes. There was no rest between the different submaximal levels. $VO_2$ was continuously measured with the AMIS 2001. At the end of each submaximal level capillary blood was taken from the fingertip and later analysed for [Hla]. At every work rate the subjects rated their perceived exertion on the Borg's RPE-scale (BORG, G. Perceived exertion as an indicator of somatic stress. Scand J Rehabil Med. 1970, vol. 2, no. 2, p. 92-8), both central and muscular exertions were rated. After eight minutes of recovery, the subject was instructed to cycle for as long as possible at a work rate corresponding to his calculated maximal oxygen uptake (ÅSTRAND, P-O, et al. Textbook in work physiology. McGraw-Hill, 1970. ISBN 0070024065. p. 619). During this test the subjects actual $VO_2$peak was measured and if the subject was able to cycle for longer than seven minutes extra power of 20-30 watts was added every minute until exhaustion. One and three minutes after the maximal test capillary blood were sampled from the fingertip for analysis of [Hla].

Before the second pre-test, the submaximal levels were adjusted so that they corresponded to 45, 60, 70, 80 and 85% of $VO_2$peak. The maximal work rate was also adjusted, if necessary, so that the time to exhaustion was kept between four and seven minutes.

The main tests: The subjects refrained from heavy exercise three days prior to the main tests and avoided all exercise the day before the tests. They were also told to eat their last light meal at least 3 hours before the start of the tests. When the subjects came to the laboratory they received their last dose of either placebo or nitrate and were allowed to rest in the supine position for 60 minutes before the test commenced.

All subjects used a standardized warm up procedure of five min of cycling at 100 watts followed by five minutes of rest. The submaximal and maximal tests were performed in the same way as the second pre-test with five submaximal work rates lasting five minutes each, without rest between the different levels. Identical work rates were used during the two main tests. Venous blood (9 ml) was drawn at rest 45 minutes after the last nitrate/placebo-dose was ingested and again immediately after the $VO_2$peak-test. The blood was placed in an ice bath and centrifuged within five minutes at 1300 rpm and 4° C. The plasma was separated and kept at −80° C. until it was analyzed for its nitrate and nitrite concentrations by a chemiluminescence assay as described previously (LUNDBERG, J O, et al. Inorganic nitrate is a possible source for systemic generation of nitric oxide. Free Rad Bio Med. 2004, vol. 37, no. 3, p. 395-400).

Statistics and calculations: Results are expressed as means t standard deviation (mean±SD). Paired t-tests were used to evaluate the difference between the nitrate and the placebo trials. The significance level was set as p≤0.05.

Gross efficiency (GE) was defined as the work rate divided by the actual energy expenditure (EE). The EE was in turn calculated with the Brouwer equation (BROUWER, E. On simple formulae for calculating the heat expenditure and the quantities of carbohydrate and fat oxidized in metabolism of men and animals, from gaseous exchange (Oxygen intake and carbonic acid output) and urine-N. Acta Physiol Pharmacol Neerl. 1957, no. 6, p. 795-802). Delta efficiency (DE) was defined as the increase in work rate divided by the increase in EE (GAESSER, G A, et al. Muscular efficiency during steady-rate exercise: effect of speed and work rate. J Appl Physiol. 1975, no. 38, p. 1132-1139). The DE was based on the four lowest work rates and was analyzed with linear regression. The oxygen pulse is defined as $VO_2$/HR.

B. Results

Blood pressure at rest: Average resting systolic blood pressure was lower after nitrate supplementation (112±8 mmHg) compared to placebo (120±5.9, p<0.01). The diastolic blood pressure was also lower after nitrate (68±5.5 mmHg) compared to placebo (74±6.8 mmHg, p<0.01). Parts of these findings have been published as a separate communication (Larsen et al. 2006).

Blood values: No change was observed in [Hb] at rest (NIT 152±11, CON 153±11 g×l⁻¹, p=0.87) or immediately after the $VO_2$peak-test (NIT 163±13, CON 161±13 g×l⁻¹, p=0.27). Nor were there any change in the hematocrit value at rest (NIT 42±4, CON 43±3%, p=0.19) or after the $VO_2$peak-test (NIT 46±4, CON 47±4%, p=0.6).

Plasma levels of nitrate at rest were 27±6.9 μM in CON and 182±55 in NIT (p<0.01). Nitrate levels immediately after the maximal work test were 29±6.1 in CON and 175±61 μM in NIT (p≤0.01). Plasma nitrate did not change during exercise either in NIT or in CON (p=0.8). Nitrite levels at rest were 124±28 in CON and 226±87 nM in NIT (p≤0.01). Immediately after the maximal work test the nitrite levels were 111±29 in CON and 137±48 in NIT (p=0.17).

Figure 6:
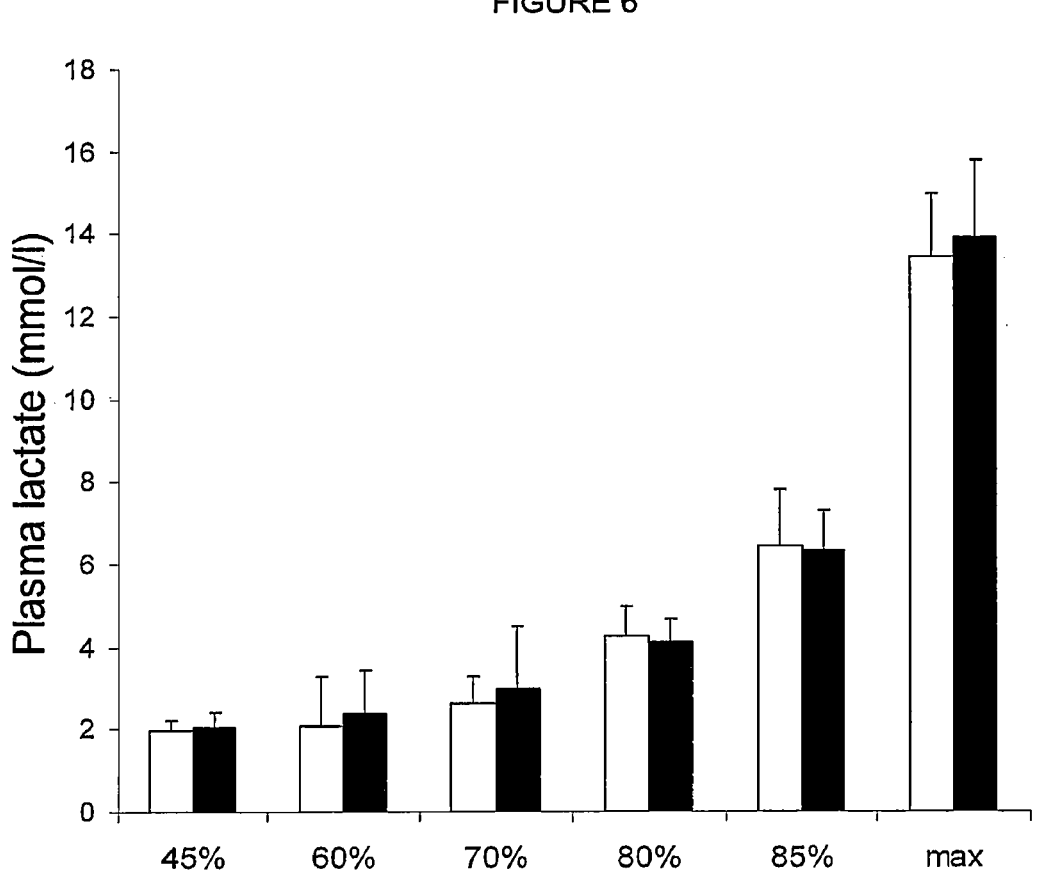
FIG. 6 is a bar diagram showing plasma lactate concentration measured at 6 different work rates after dietary supplementation with sodium nitrate (0.1 mmol/kg body weight/day for 3 days, filled bars) or an equal amount of sodium chloride (placebo, empty bars).

The decrease in nitrite concentrations during exercise was more pronounced in NIT than in CON (FIG. 6). The increase in c-GMP concentrations after the maximal work as compared to rest tended to be higher in NIT than in CON (p=0.08).

Blood pressure: Average resting systolic blood pressure decreased from 120+/−5.9 after NIT to 112±8 mmHg after CON (p=0.003). The diastolic blood pressure decreased from 74 t 6.8 to 68±5.5 mmHg in the CON and NIT-groups respectively (p=0.005). Parts of these findings have been published as a separate communication (LARSEN, F J, et al. Effects of dietary nitrate on blood pressure in healthy volunteers. N Engl J Med. 2006, vol. 355, no. 26, p. 2792-3).

Figure 5:
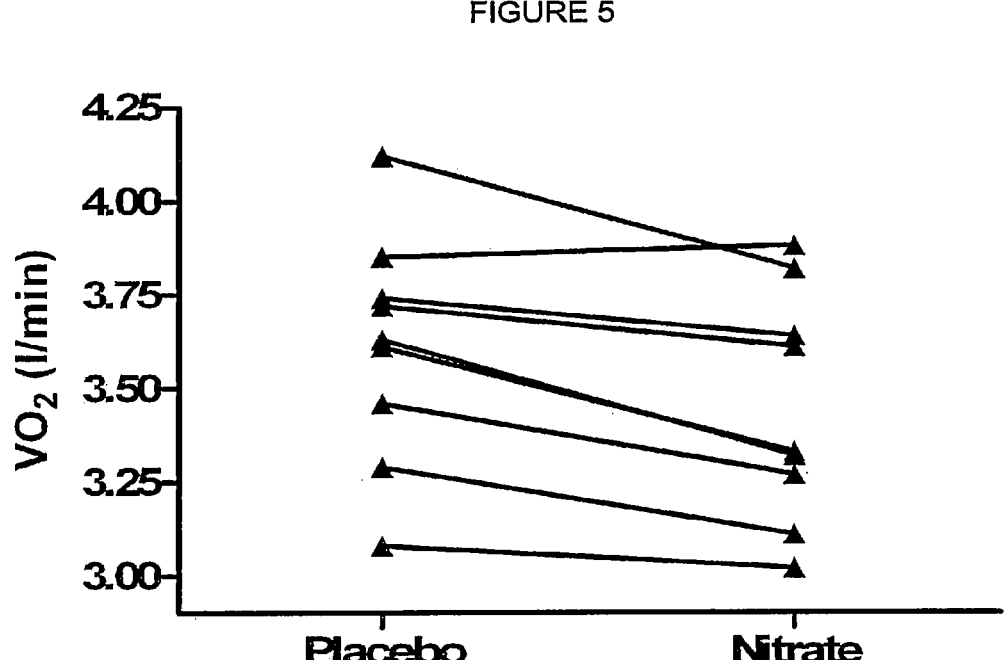
FIG. 5 is a graph showing oxygen consumption during bicycle exercise at 80% of $VO_2$peak in 9 healthy male volunteers. Measurements were made after a 3-day dietary supplementation with sodium nitrate (0.1 mmol/kg body weight/day) or an equal amount of sodium chloride (placebo). The difference between nitrate and placebo periods was significant ($p<0.01$).

Submaximal work parameters: After nitrate administration $VO_2$ was significantly lower during the four work rates corresponding to 45-80% $VO_2$peak compared to the placebo period (FIG. 5). The most significant difference was seen at 80% of $VO_2$peak (NIT 3.44±0.311×min⁻¹ vs CON $3.61 \pm 0.311 \times \text{min}^{-1}$, p=0.003, FIG. 5). On average $VO_2$ was $0.151 \times \text{min}^{-1}$ lower in the NIT-trials over the 4 submaximal work rates. There was no difference in heart rate (HR) between the NIT and CON-trials (see FIG. 6). The oxygen pulse tended to decrease from 21.0 t 2.0 during CON to $20.3 \pm 1.9$ ml×beat$^{-1}$ (p=0.08). No significant differences changes were found between NIT and CON in [Hla] (FIG. 6), $V_E$, $V_E$/VO2 or respiratory exchange ratio (RER) during any of the submaximal work rates. The average Gross efficiency (GE) is defined as the work rate divided by the actual energy expenditure (EE). The EE was in turn calculated with the Brouwer equation (Brouwer, supra). GE gross efficiency improved from 19.7% during CON to 21.1% during NIT (p=0.02). Delta efficiency (DE) is the increase in workload divided by the increase in EE (Gaesser & Brooks, supra). The DE is in this case based on the four lowest work rates, which were analyzed with a linear regression analysis. The DE Delta efficiency (DE) increased significantly from $22.1 \pm 1.6\%$ during CON compared to $22.9 \pm 1.9\%$ during NIT, (p=0.04).

Maximal work capacity: There was no significant difference in the $VO_2$peak between the NIT and CON trials ($4.49 \pm 0.44$ and $4.61 \pm 0.281 \times \text{min}^{-1}$ respectively, p=0.29). These values were also not significantly different from the $VO_2$peak achieved during the pre-test ($4.54 \pm 0.321 \times \text{min}^{-1}$). Likewise, no significant differences were noted either in $V_{Emax}$ (NIT $182 \pm 21.4$ vs CON $186 \pm 21.71 \times \text{min}^{-1}$, p=0.5), HR.sub.max (NIT $189.8 \pm 7.0$ vs CON $190.3 \pm 7.5$ beats×min$^{-1}$, p=0.94) or maximal work rate (NIT $360.6 \pm 32.8$ vs CON $358.9 \pm 32.3$ watt, p=0.35). There was no difference between NIT and CON in the rating of perceived exertion (Borg RPE-scale) at any work load (submax or max).

Comment to the results: In the present study a significantly reduced oxygen demand at submaximal workloads was noted after nitrate administration was noted at the four lowest workloads. The fifth work rate, at approximately 85% $VO_2$peak, was well above the lactate threshold in several subjects and thus the anaerobic energy production became more pronounced. This led to involvement of accessory muscle groups and a noticeably change in motion pattern. At this work rate the $VO_2$ did not reach a stable steady-state level and is therefore unsuitable for the calculation of muscular efficiency. The reason for including this fifth work rate in the protocol was to receive a lactate value above the lactate threshold and thereby get an indication of changes in the upper part of the lactate curve.

3. Oral Sodium Nitrate and Glucose Homeostasis

Figure 7A:
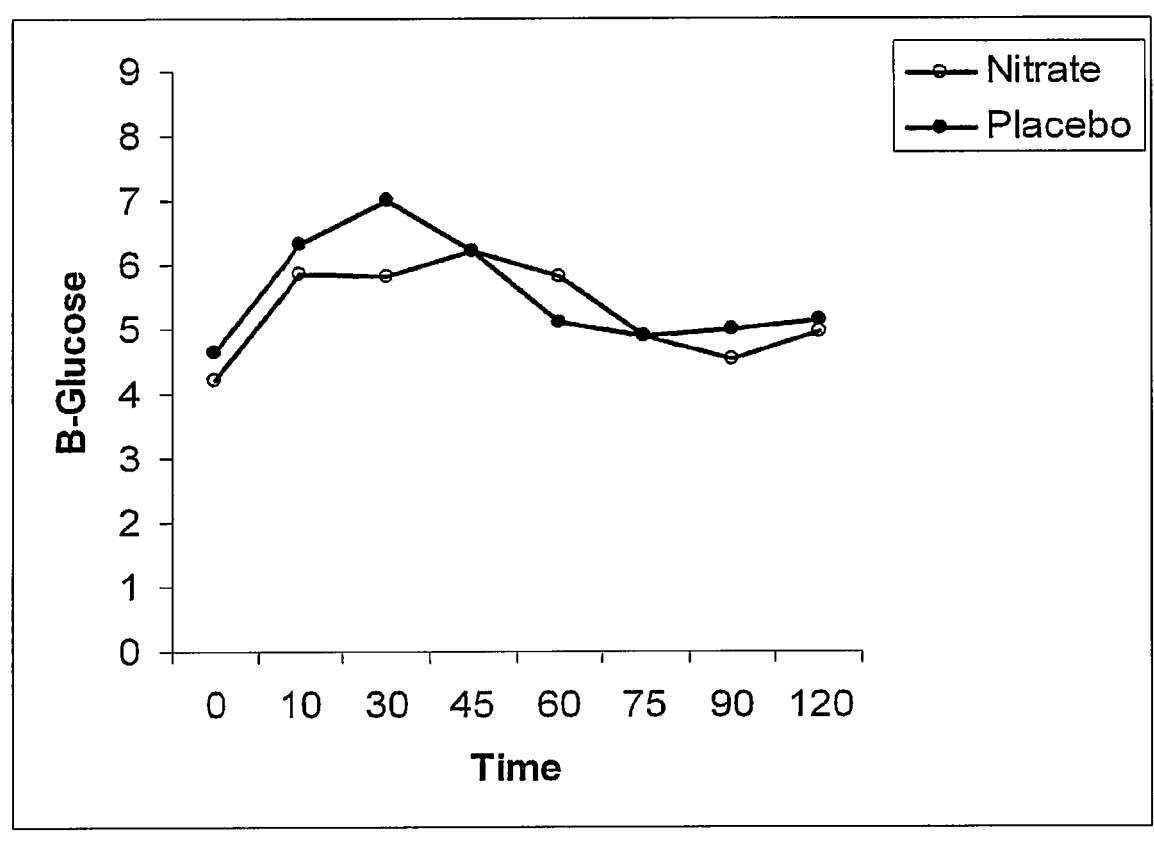
FIGS. 7a-7c consist of three graphs, showing changes in blood glucose levels after an oral challenge with glucose for three test subjects in a double-blind, placebo-controlled cross-over study (FIGS. 7a, 7b and 7c). A standard oral glucose tolerance test was performed. The subjects (healthy non-smoking volunteers) had their diet supplemented for 3 days with either sodium chloride (placebo) or sodium nitrate (Nitrate) at a dose of 0.1 mmol/kg body weight/day.
Figure 7B:
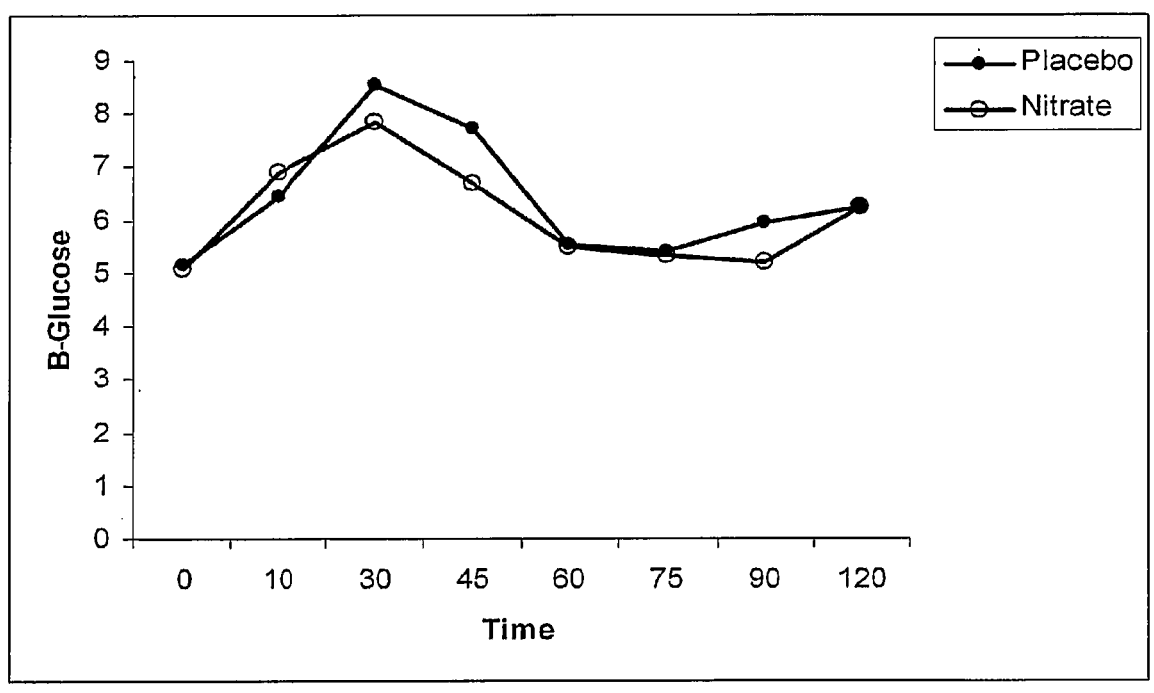
Figure 7C:
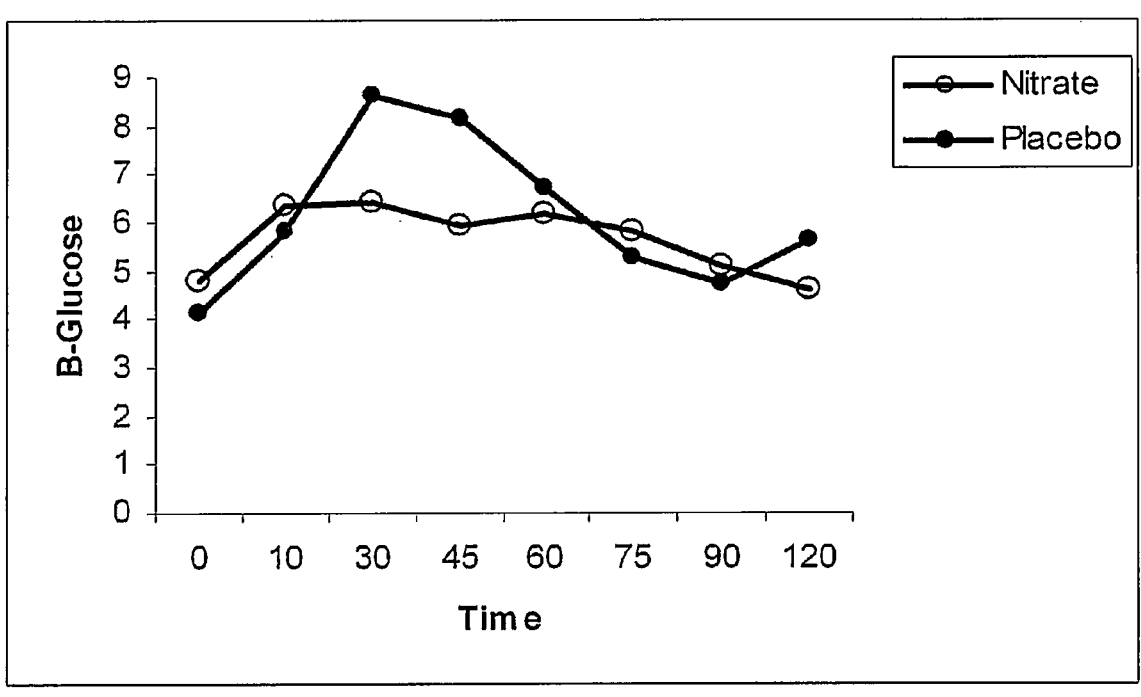

The increase in plasma glucose after a standard Oral Glucose Tolerance Test (75 g glucose in 250 ml water) is lower when measured after nitrate pre-treatment (1 mmol/kg body weight $NaNO_3$) compared to placebo (NaCl). The study was performed with three healthy test subjects in a double-blind study. Glucose ingestion started 60 min after the nitrate ingestion. Blood glucose levels were measured during the 120 min period after the glucose load (n=3). At 30 min mean plasma glucose was 8.2 mmol/l with placebo and in the same subjects 6.5 mmol/l after nitrate supplementation. The results are shown in FIGS. 7a, b, and c.

Figure 8:
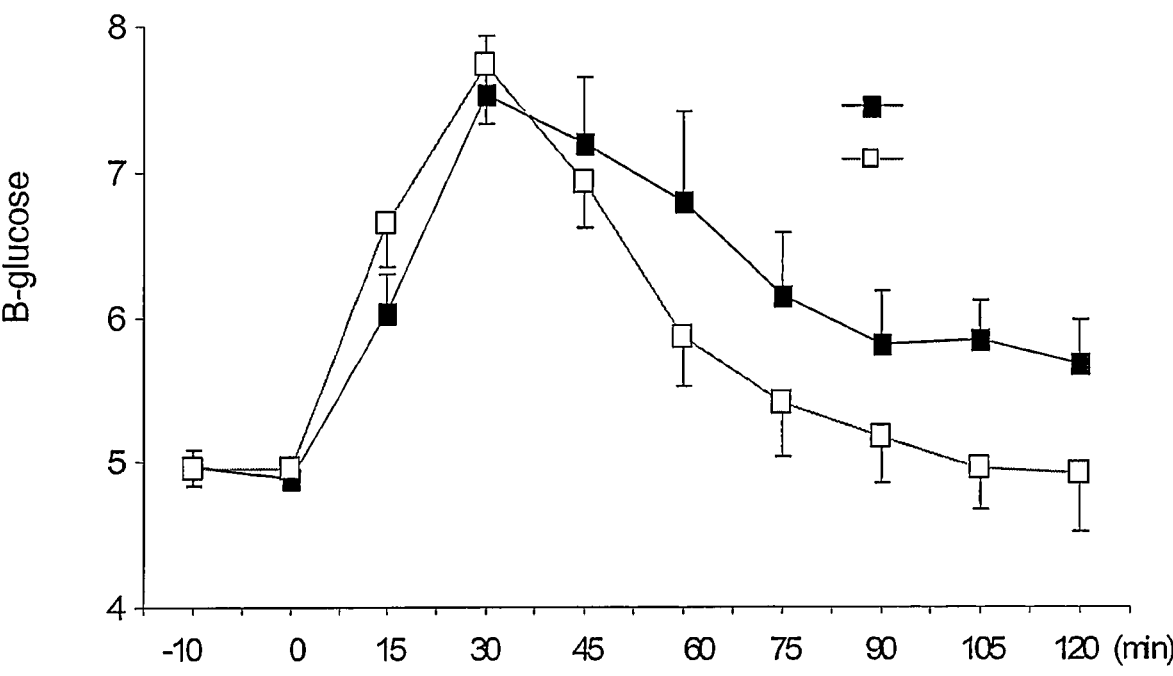
FIG. 8 is a graph showing changes in blood glucose levels after an oral challenge with glucose in 8 additional subjects in a double-blind, placebo-controlled cross-over study. A standard oral glucose tolerance test was performed. The subjects (healthy non-smoking volunteers) had their diet supplemented for 3 days with either sodium chloride (PLACEBO) or sodium nitrate (NITRATE) at a dose of 0.1 mmol/kg/day. Data are presented as mean t SEM.

The lower increase in plasma glucose after nitrate pre-treatment was verified in a further study wherein a standard Oral Glucos Tolerance Test (75 g glucose) was performed in 8 healthy non-smoking subjects after a three-day supplementation with either sodium chloride or sodium nitrate at equal molar amounts (0.1 mmol/kg body weight/day). The study had a double-blind, placebo-controlled, cross-over design. Blood glucose levels were measured at two time points before (−10 and 0 min) and at 15, 30, 45, 60, 75, 90, 105 and 120 min after glucose intake (n=8). At the occasion when the subjects had taken nitrate, the area under the curve for blood glucose was smaller compared to when they had ingested placebo. The results are shown in FIG. 8 as mean SEM.

4. Effect of Ingestion of Beetroot on Blood Pressure

A 43-year-old non-smoking subject with hypertension ingested fresh beetroot juice (300-400 md/day) for 14 days. The blood pressure was measured twice a day for 14 days and then twice on day 20 (counted from day 1 of treatment). The Basal blood pressure was 142/99 on the day when the experiment started.

Figure 9:
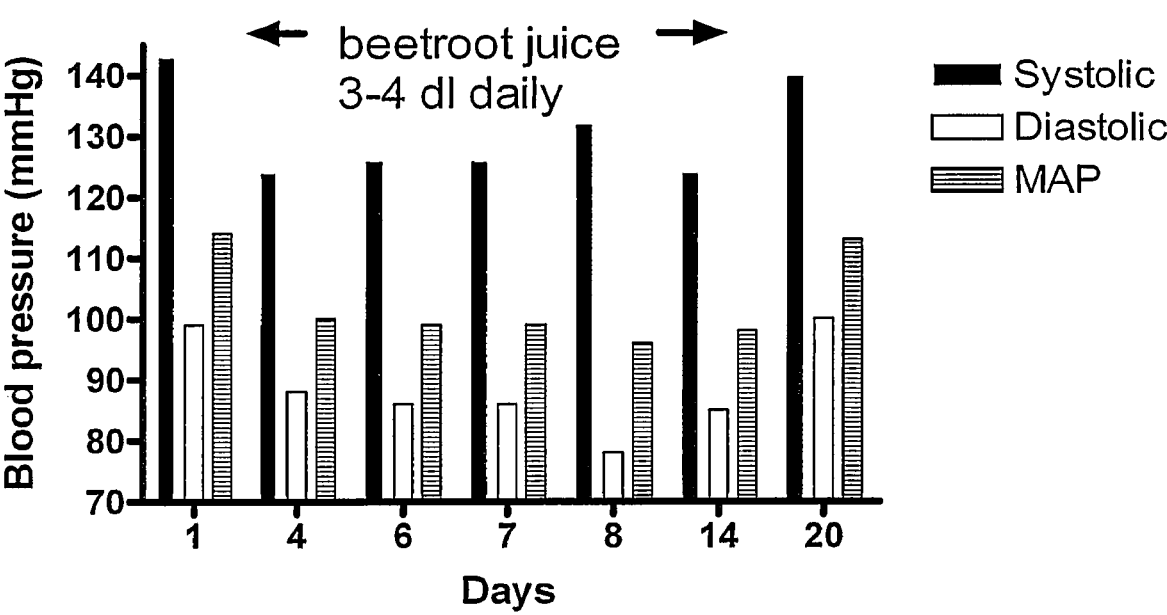
FIG. 9 is a graph showing the effect of a two-week intervention with beetroot juice (fresh juice 3-4 dl/day) on systolic, diastolic and mean arterial (MAP) blood pressure in a 43-year-old male with hypertension.

The results from the ingestion of beetroot juice are shown in FIG. 9. The mean of the two daily measurements are shown in the bars. With ingestion of the beetroot juice (between day 1-14) a mean reduction in systolic pressure of ≅15 mmHg and a mean reduction in diastolic pressure of ≅16 mmHg was seen. When measured again 6 days after stopping beetroot juice treatment (day 20), the blood pressure had increased to basal levels (140/100). Pulse rate was unchanged throughout the experimental period. MAP=mean arterial pressure.

5. Concentrations of Plasma Nitrite after Intravenous Infusion of Nitrate

A. Methods

Anesthetized rats (n=11) were given a bolus dose (10 mg/kg body weight) of NaNO.sub.3 (open boxes) and blood samples were collected at indicated time points. 7 additional rats were pre-treated with 30 mg/kg body weight of allopurinol given intra peritoneally 60 minutes prior to the NaNO.sub.3 infusion (closed triangles) and blood samples were collected at the time points indicated. Allopurinol inhibits the xanthine oxidase, an enzyme suggested being involved in the reduction of nitrate to nitrite in mammal cells. Plasma was extracted and analyzed for nitrate and nitrite.

Three different strains of mice—wild type (n=5 placebo, n=5 nitrate), germ free (n=5 placebo, n=5 nitrate) and eNOS knockout mice (n=2 placebo, n=3 nitrate), were given an intra peritoneal injection of 10 mg/kg body weight nitrate or placebo (NaCl) and plasma level of nitrite measured 1 hour later.

B. Results

Figure 10:
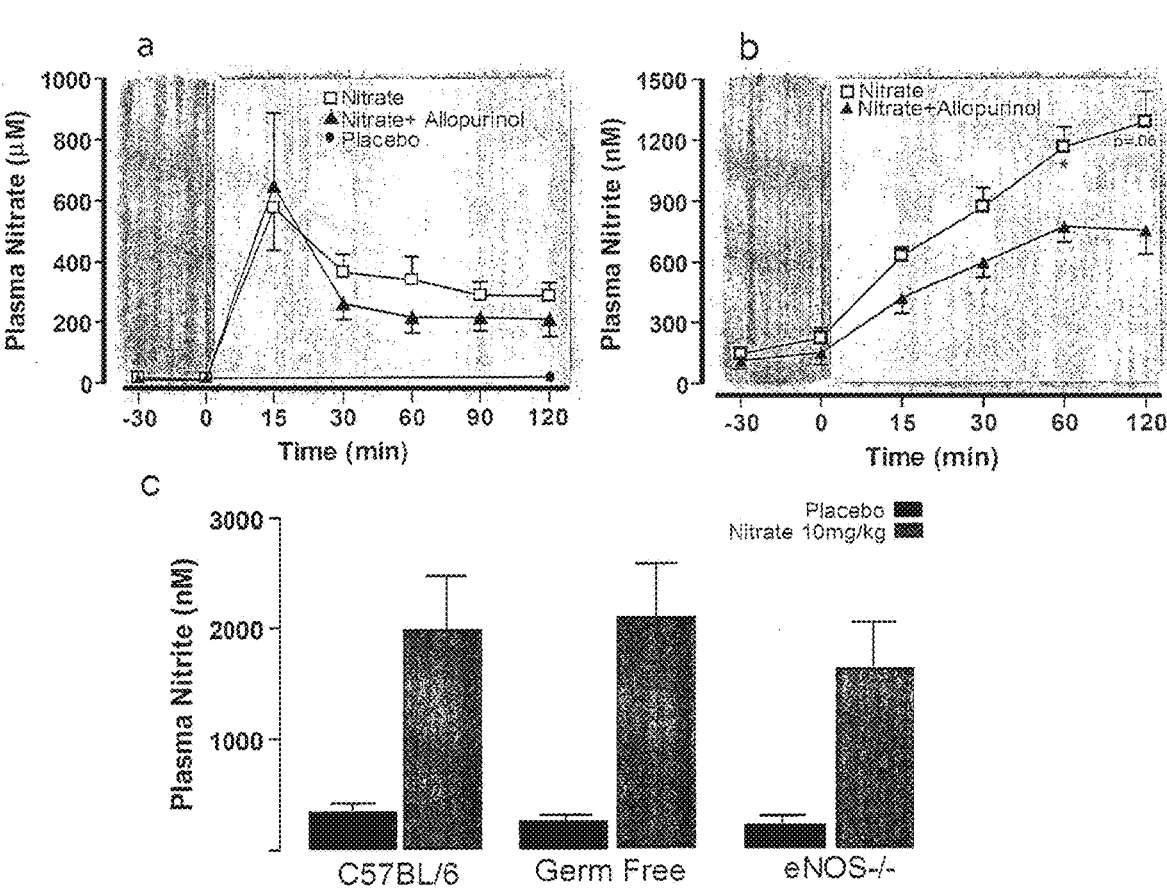
FIG. 10 shows the plasma nitrate and nitrite concentrations after intravenous infusion of nitrate. Panel a) shows plasma nitrate concentration; panel b) shows plasma nitrite concentrations; and panel c) shows plasma nitrite concentrations in wild type (C57BL/6), germ free and knockout (eNOS) mice.

The results from the intravenous infusion of nitrate are shown in FIG. 10 a-c. FIG. 10 panel a shows the plasma nitrate concentration and FIG. 10 panel b shows the plasma nitrite concentration. After infusion of nitrate the concentration of plasma nitrate increases dramatically both in rats that received nitrate and rats that received nitrate+allopurinol (a). The plasma nitrite concentrations increased in rats that received nitrate as well as in rats that received nitrate+ allopurinol, (b). However the increase in the rats that received only nitrate was significantly greater, *p<0.05.

FIG. 10 panel c shows that nitrate-induced increase in plasma nitrite is equal in wild type (n=5 placebo, n=5 nitrate), germ free (n=5 placebo, n=5 nitrate) and eNOS knockout mice (n=2 placebo, n=3 nitrate), p=0.05*.

Previously it has been suggested that only bacterial cells and not mammalian cells can reduce nitrate to nitrite. These results surprisingly show that also mammalian cells can metabolize nitrate to nitrite. Further, they suggest that the xanthine oxidase enzyme is involved in the reduction of nitrate to nitrite.

6. Enhancement of Post-Ischemic Blood Flow

Rats received an intravenous bolus dose of 10 mg/kg nitrate (NaNO$_3$, n=4) or placebo (NaCl, n=4)) diluted in PBS (pH 7.4) followed by continuous infusion of 3 mg/kg body weight/h. An hour after the addition of nitrate (open boxes) or placebo (filled circles), L-NAME (50 mg/kg) was given, and 10 minutes later, a supra renal clamping of the abdominal aorta was performed. After 30 minutes of ischemia the clamp was removed and the abdominal aortic blood flow was monitored during 60 minutes.

Figure 11:
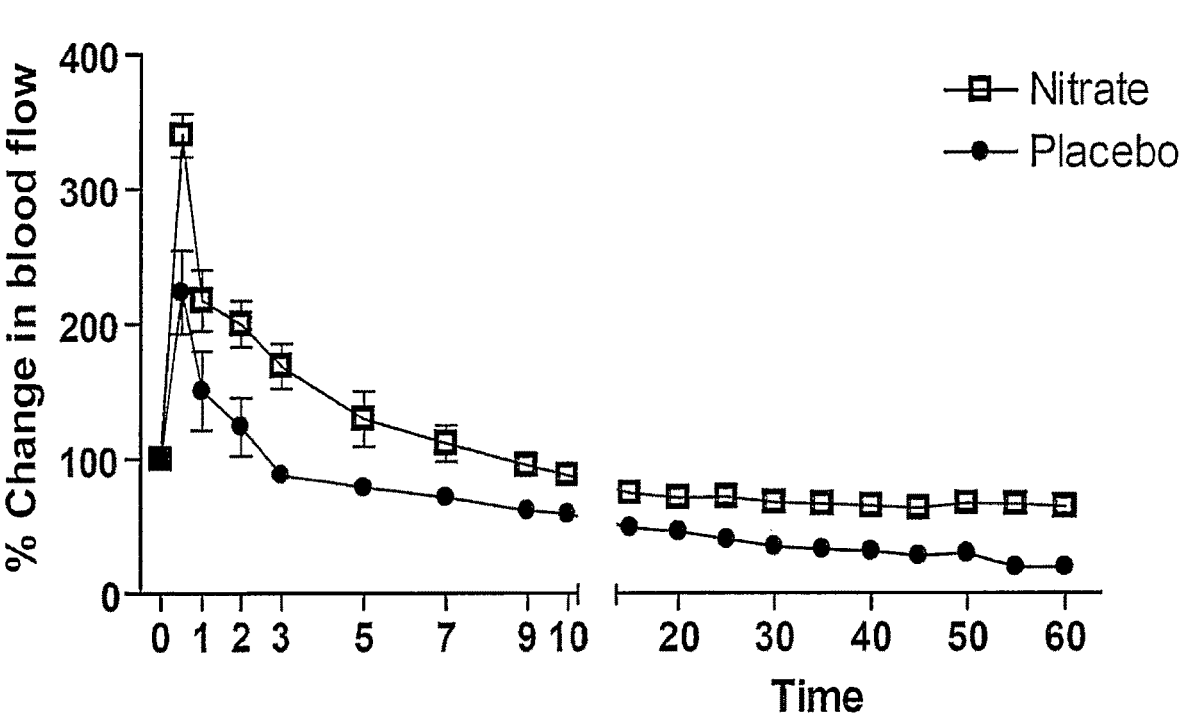
FIG. 11 is a graph showing enhanced post-ischemic blood flow after nitrate infusion.

The results show that the nitrate-treated rats maintain a higher blood flow during the early (0-10 minutes) as well as the late (10-60 minutes) post-ischemic phase compared to the placebo treated rats (FIG. 11). Remarkably, after 60 min of reperfusion the blood flow had decreased to only 20% of pre-ischemic values in the control rats, while in the nitrate-treated rats, the blood flow was maintained at almost 75% of control values. This demonstrates a strong augmentation of the nitrate-nitrite-NO pathway during an ischemic event.

The invention claimed is:

1. A method of administering nitrate to cause a beneficial systemic effect in a human subject in need thereof, the method comprising administering to the human subject at least 0.01 mmol/kg/day of nitrate, wherein the systemic beneficial effect is observable in blood pressure, oxygen demand, glucose homeostasis, and/or blood flow.

2. The method of claim 1, wherein the nitrate is administered at a dose of 0.01 mmol/kg/day to 1.0 mmol/kg/day.

3. The method of claim 2, wherein the amount of nitrate is administered in a single dose.

4. The method of claim 2, wherein the amount of nitrate is administered in multiple doses per day.

5. The method of claim 4, wherein the amount of nitrate is administered in three doses per day.

6. The method of claim 2, wherein at least one dose of nitrate is administered before the onset of exercise.

7. The method of claim 6, wherein the dose of nitrate is administered at about 60 minutes before exercise.

8. The method of claim 1, wherein the amount of nitrate is at least 0.1 mmol/kg/day.

9. The method of claim 1, wherein the beneficial effect is selected from the group consisting of: reduction in oxygen consumption, increase in endurance, increase in muscular efficiency, reduction in the oxygen cost of exercise, reduction in blood pressure, increase in vasodilation, increase in muscle blood flow, reduction of systolic blood pressure, reduction of diastolic blood pressure, and reduction of mean arterial blood pressure.

10. The method of claim 1, wherein the beneficial effect is amelioration of a disease or condition associated with increased metabolic rate and/or oxygen consumption.

11. The method of claim 10, wherein the disease or condition is selected from the group consisting of: surgical stress, malnutrition, burn injury, premature birth, anorexia, happenstance of organ transplantation, fasting hyperglycemia, impaired fasting glucose, impaired glucose tolerance, insulin resistance, reduced HDL cholesterol, elevated triglycerides, elevated uric acid, obesity, cancer with anorexia, diabetes, stroke, hypertension, hyperthyreosis, cardiac arrest, myocardial infarction, sleep apnea syndrome, organ ischemia, chronic obstructive pulmonary disorder, fever, and asthma.

12. The method of claim 10, wherein the disease or condition is impaired glucose tolerance.

13. The method of claim 10, wherein the disease or condition is diabetes.

14. The method of claim 10, wherein the disease or condition is reduced HDL cholesterol.

15. The method of claim 10, wherein the disease or condition is elevated triglyceride.

16. The method of claim 10, wherein the disease or condition is obesity.

17. The method of claim 10, wherein the disease or condition is fever.

18. The method of claim 10, wherein the disease or condition is asthma.

19. The method of claim 1, wherein administering to the human subject at least 0.01 mmol/kg/day of nitrate does not cause methemoglobin formation to result in greater than 10% methemoglobin in the subject.

20. The method of claim 1, wherein administering to the human subject at least 0.01 mmol/kg/day of nitrate does not cause methemoglobin formation to result in greater than 5% methemoglobin in the subject.

21. The method of claim 1, wherein administering to the human subject at least 0.01 mmol/kg/day of nitrate does not cause methemoglobin formation to result in greater than 2% methemoglobin in the subject.

22. The method of claim 1, wherein administering to the human subject at least 0.01 mmol/kg/day of nitrate causes no methemoglobin formation.

23. A method of administering nitrate to cause a beneficial effect in a human subject in need thereof, said method comprising administering to the human subject between 0.01 mmol/kg/day and 100.0 mmol/kg/day of the nitrate, wherein the beneficial effect is observable in blood pressure, oxygen demand, glucose homeostasis, and/or blood flow.

* * * * *